United States Patent [19]

Doherty, III

[11] 4,213,054
[45] Jul. 15, 1980

[54] TRANSVERSE SECTION BRAIN IMAGER SCANNING MECHANISM

[75] Inventor: Edward J. Doherty, III, Halifax, Mass.

[73] Assignee: Union Carbide Corporation, New York, N.Y.

[21] Appl. No.: 866,016

[22] Filed: Dec. 30, 1977

[51] Int. Cl.² .......................... G02B 5/00; G01T 1/20
[52] U.S. Cl. .............................. 250/505; 250/363 S; 250/445 T
[58] Field of Search ............... 250/363 S, 445 T, 358, 250/366, 369, 505

[56] References Cited

U.S. PATENT DOCUMENTS 3,970,853  7/1976  Kuhl et al. .................. 250/363 S

OTHER PUBLICATIONS

Budinger, T. F. et al., "ECAT with Single-Photon and Positron Annihilation Photon Emitters", Journal of Computer Assisted Tomography, vol. 1, No. 1, 1977.
Budinger, T. F. et al., "Progress in Cardiovascular Diseases", Physics and Instrumentation, vol. XX, No. 1, Jul./Aug. 1977, pp. 19-53.
Smith, E. M., Sc.D., Maryville, Tenn., Southeastern Chapter, Society of Nuclear Medicine Continuing Education, 1976, "What is the Role of Nuclear Medicine in Medical Imaging".

Primary Examiner—Alfred E. Smith
Assistant Examiner—Janice A. Howell
Attorney, Agent, or Firm—Frederick J. McCarthy, Jr.

[57] ABSTRACT

Scanning apparatus is provided for an array of highly focused collimators surrounding a scan field.

1 Claim, 42 Drawing Figures

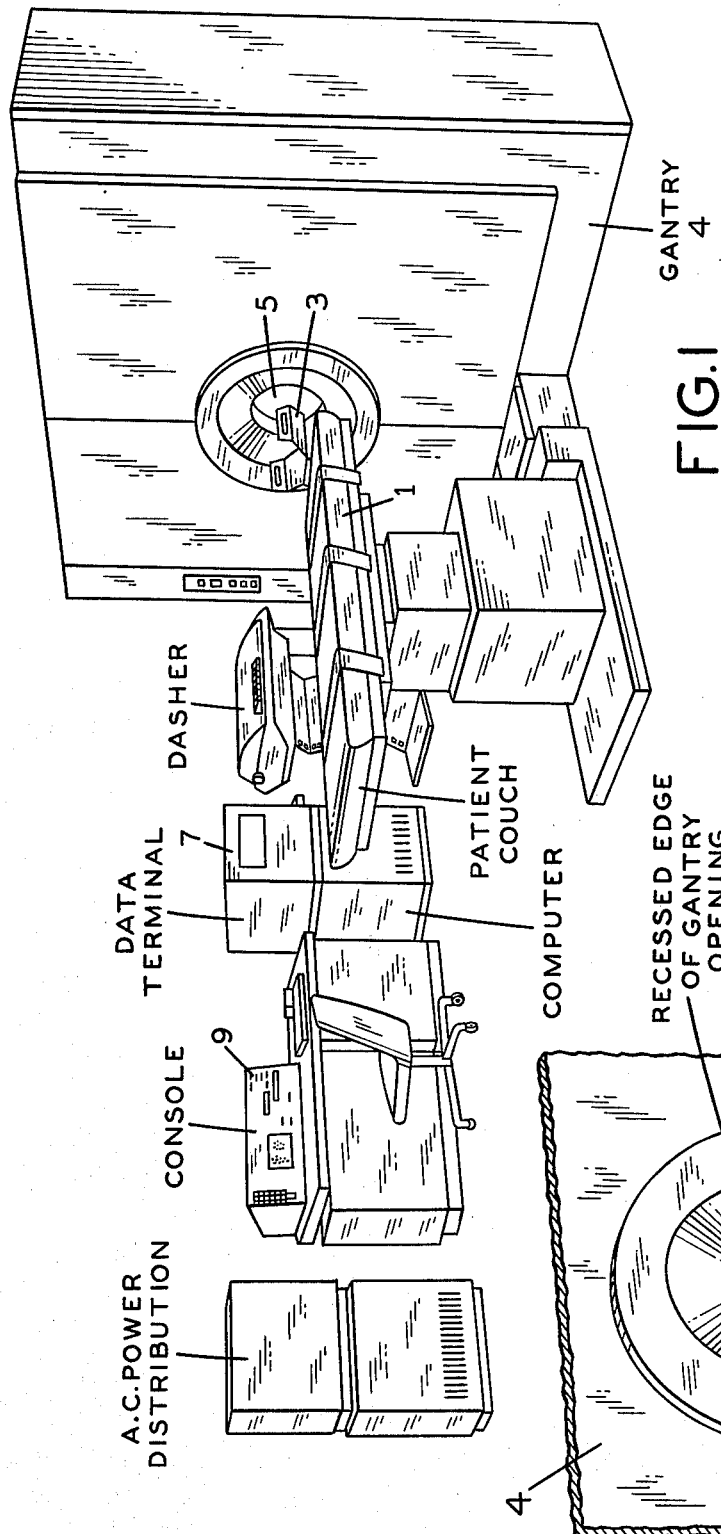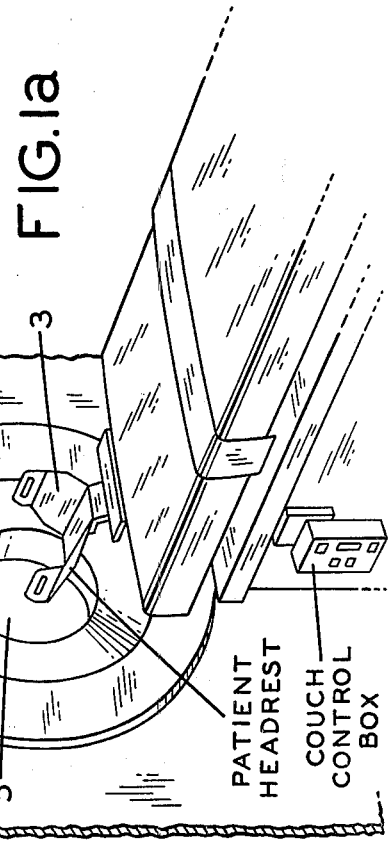

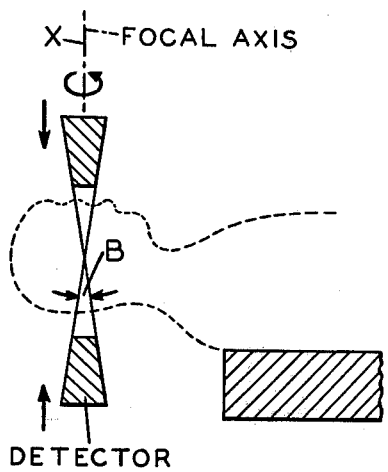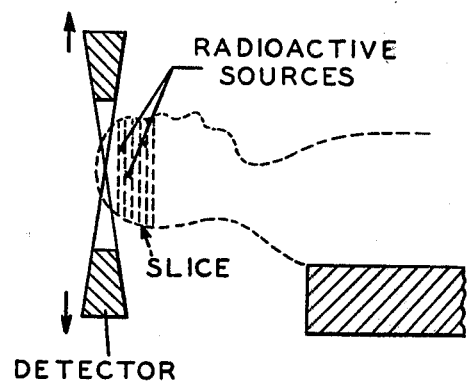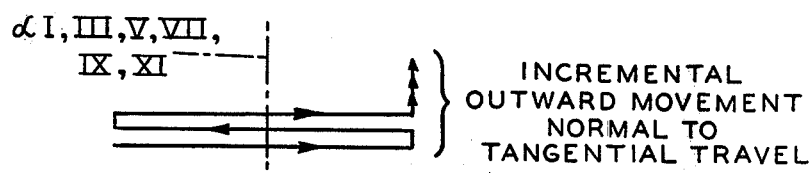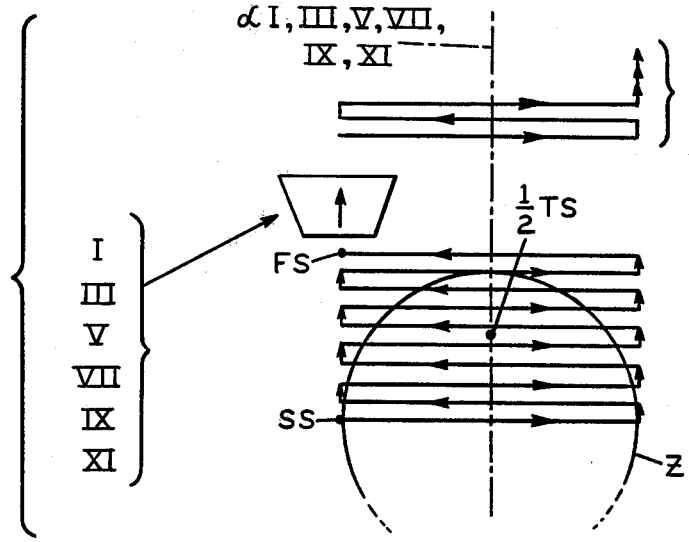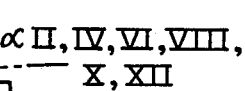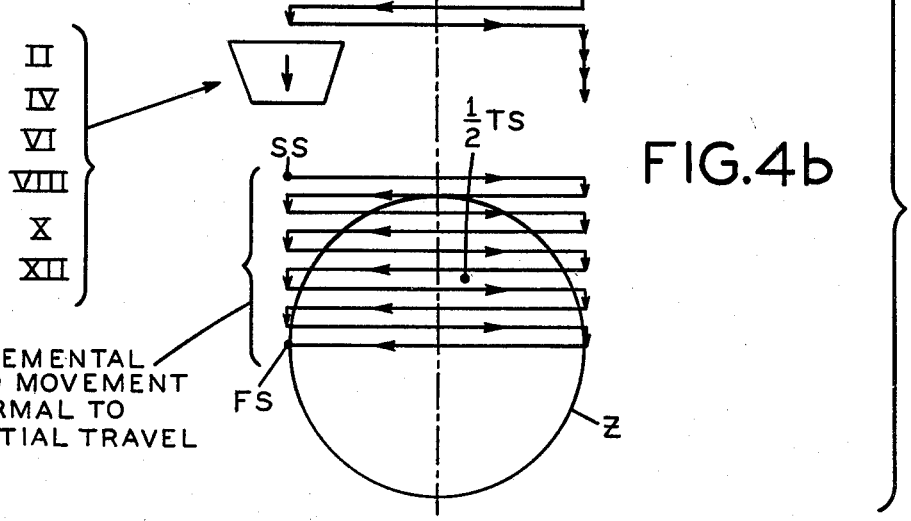

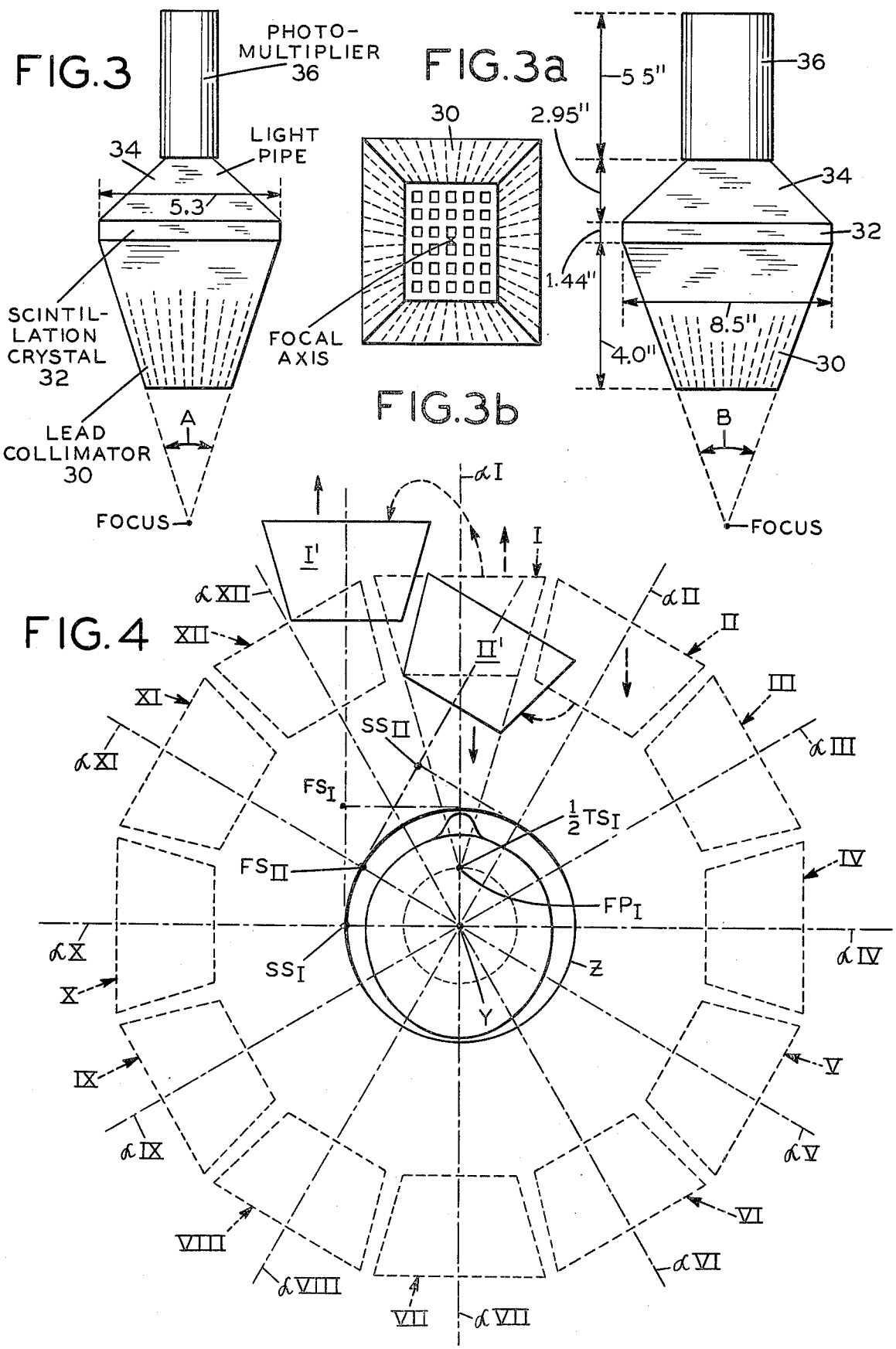

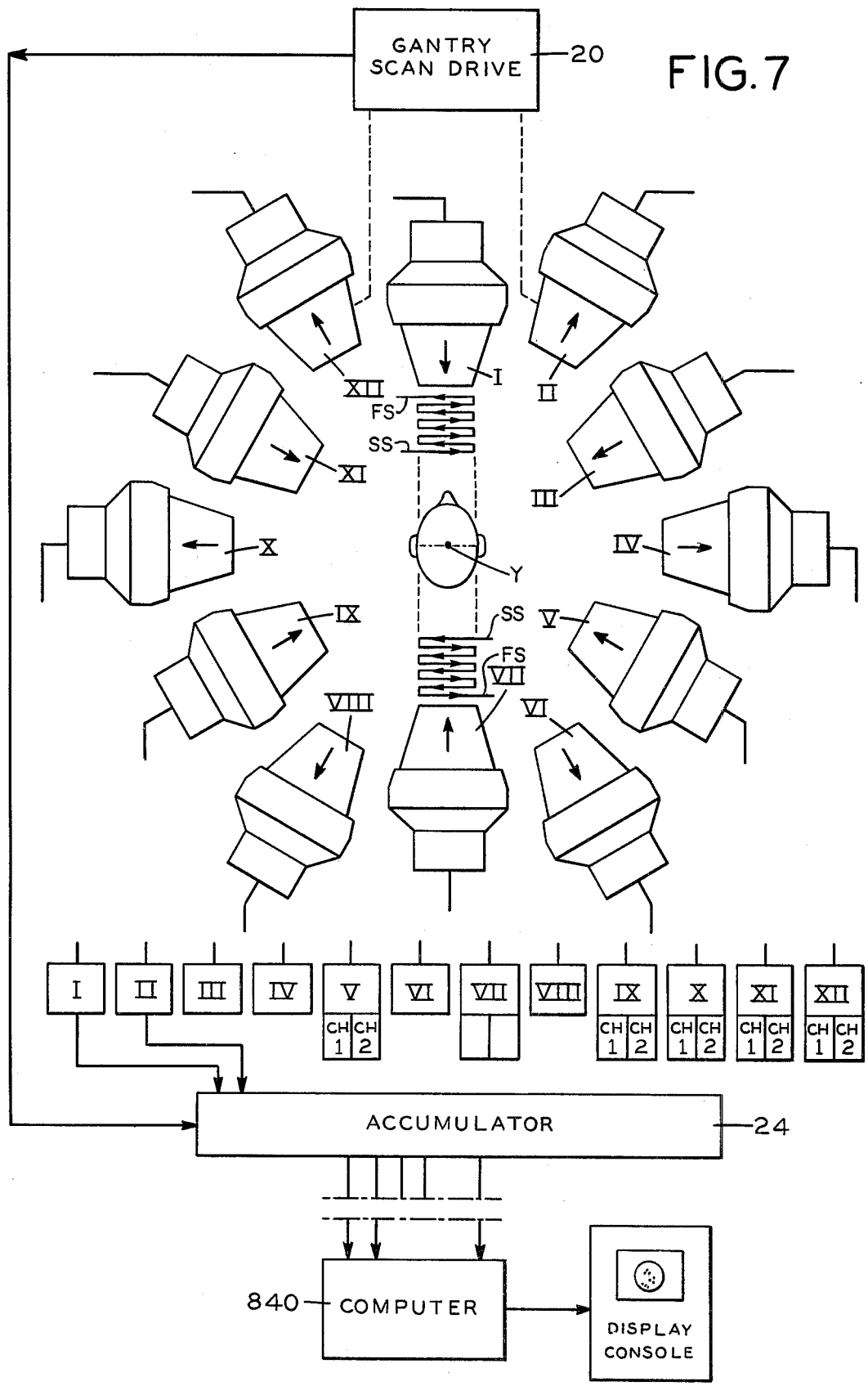

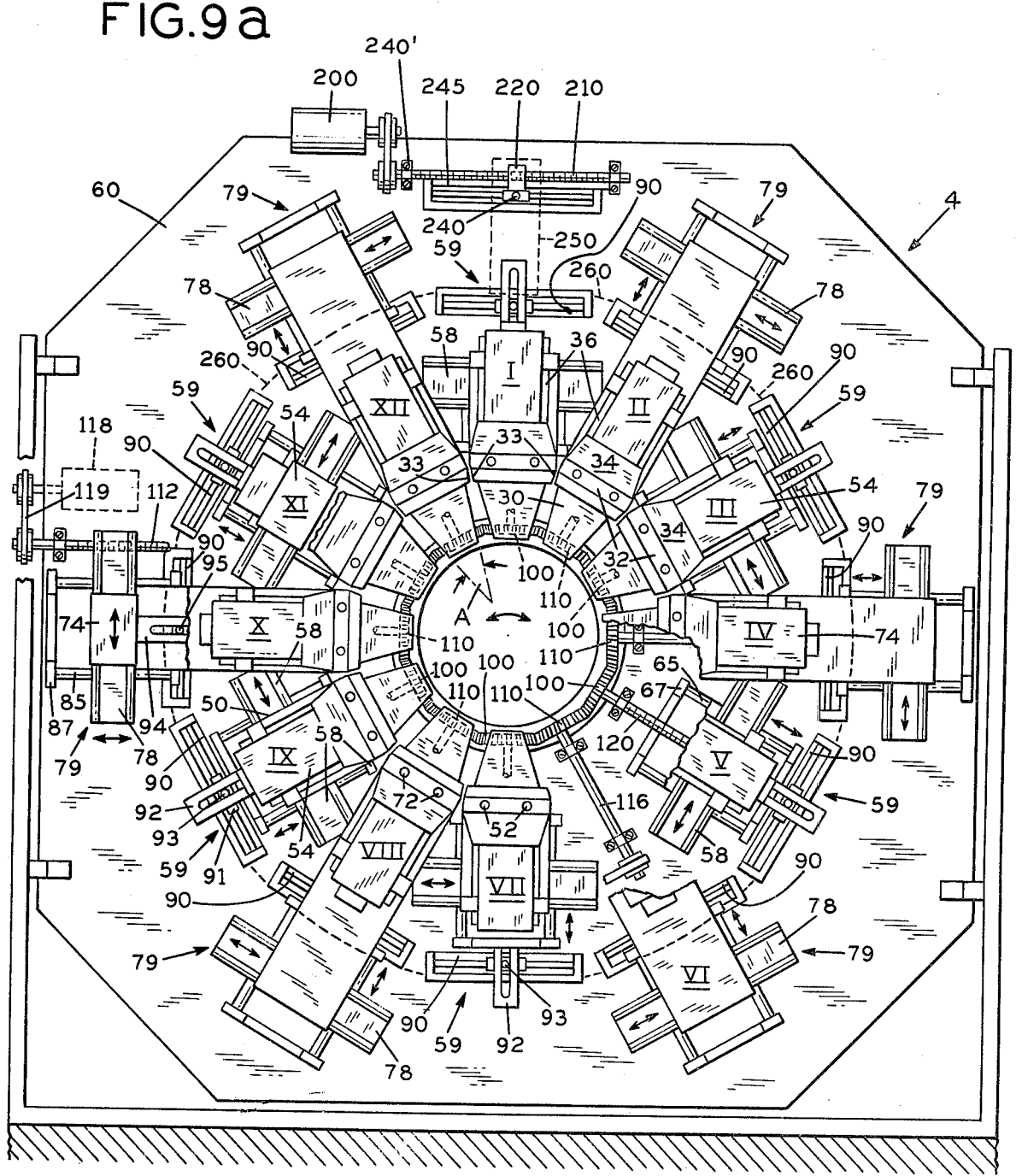

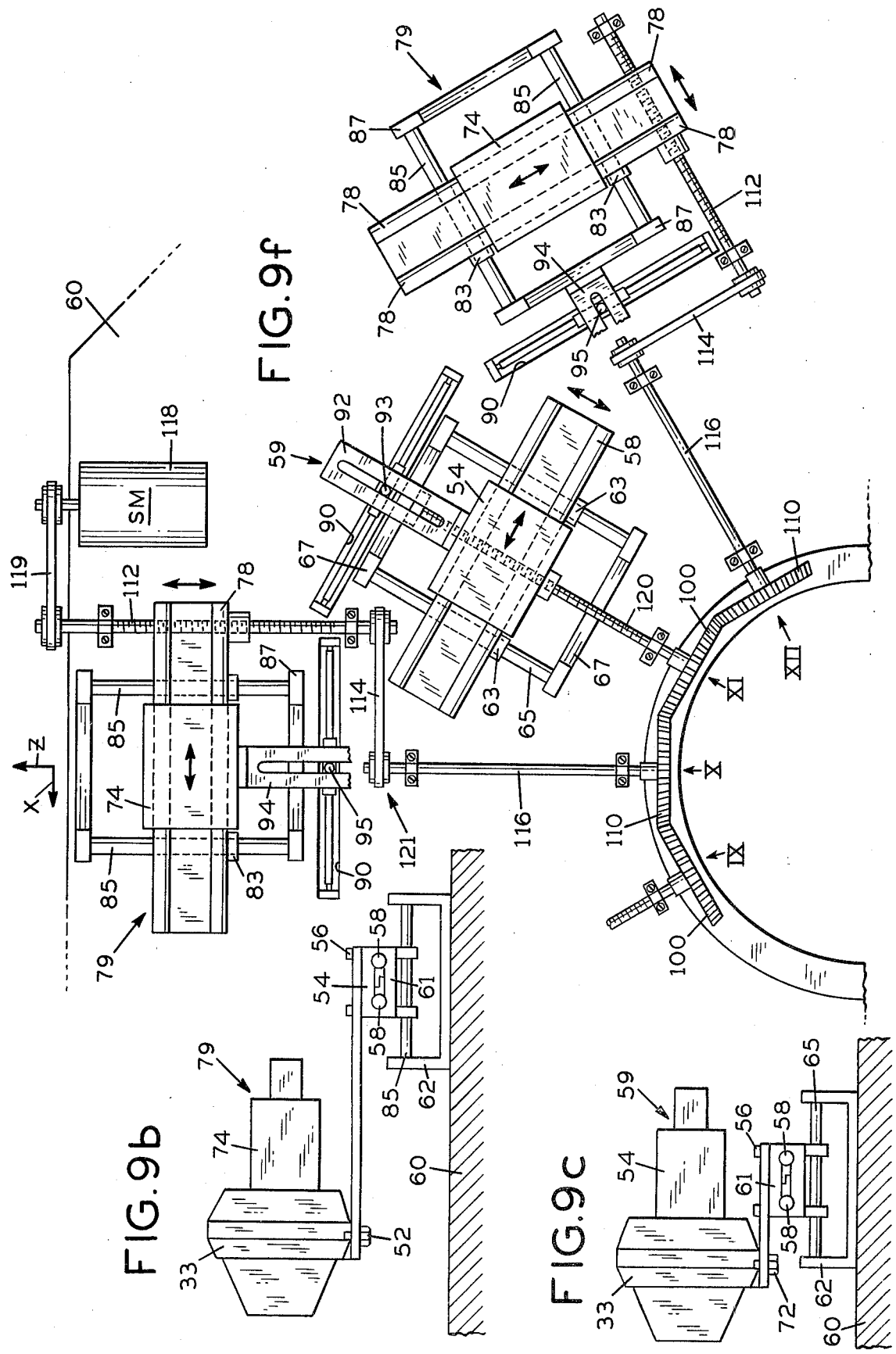

EXEMPLARY DETECTOR SAMPLING SEQUENCE
4.8 ÷ 12 μ SECONDS

TO MOTOR DRIVER 839, 849

| DET. SEQ. | R.E. | ADDR. LOC. | | LOAD SEQ. |
|---|---|---|---|---|
| 1 | I | 1<br>2<br>↓<br>128 | 4001<br>4002<br>↓<br>4128 | A | 1<br>25 |
| 2 | VII | 128<br>↑<br>2<br>1 | 4129<br>↑<br>4255<br>4256 | B | 26<br>2 |
| 3 | II | 1<br>↓<br>128 | 4257<br>↓<br>4384 | C | 3 |
| 4 | VIII | 128<br>↑<br>1 | 4385<br>↑<br>4512 | D | 4 |
| 5 | III | 1<br>↓<br>128 | 4513<br>↓<br>4640 | E | 5 |
| 6 | IX | 128<br>↑<br>1 | 4641<br>↑<br>4768 | F | 6 |
| 7 | IV | 1<br>↓<br>128 | 4769<br>↓<br>4896 | G | 7 |
| 8 | X | 128<br>↑<br>1 | 4897<br>↑<br>5024 | H | 8 |
| 9 | V | 1<br>↓<br>128 | 5025<br>↓<br>5152 | J | 9 |
| 10 | XI | 128<br>↑<br>1 | 5153<br>↑<br>5280 | K | 10 |
| 11 | VI | 1<br>↓<br>128 | 5281<br>↓<br>5408 | L | 11 |
| 12 | XII | 128<br>↑<br>1 | 5409<br>↑<br>5536 | M | 12  1536 |

CH 2

| R.E. | ADDR. LOC. | | LOAD SEQ. |
|---|---|---|---|
| A' | 1<br>↓<br>128 | 5537<br>↓<br>5664 | 13<br>27 |
| B' | 128<br>↑<br>1 | 5665<br>↑<br>5792 | 14 |
| C' | 1<br>↓<br>128 | 5793<br>↓<br>5920 | 15 |
| D' | 128<br>↑<br>1 | 5921<br>↑<br>6048 | 16 |
| E' | 1<br>↓<br>128 | 6049<br>↓<br>6176 | 17 |
| F' | 128<br>↑<br>1 | 6177<br>↑<br>6304 | 18 |
| G' | 1<br>↓<br>128 | 6305<br>↓<br>6432 | 19 |
| H' | 128<br>↑<br>1 | 6433<br>↑<br>6560 | 20 |
| J' | 1<br>↓<br>128 | 6561<br>↓<br>6688 | 21 |
| K' | 128<br>↑<br>1 | 6689<br>↑<br>6816 | 22 |
| L' | 1<br>↓<br>128 | 6817<br>↓<br>6944 | 23 |
| M' | 128<br>↑<br>1 | 6945<br>↑<br>7072 | 24  3072 |

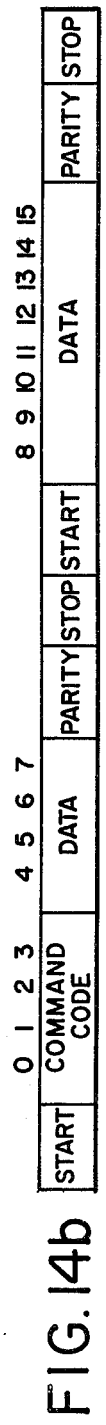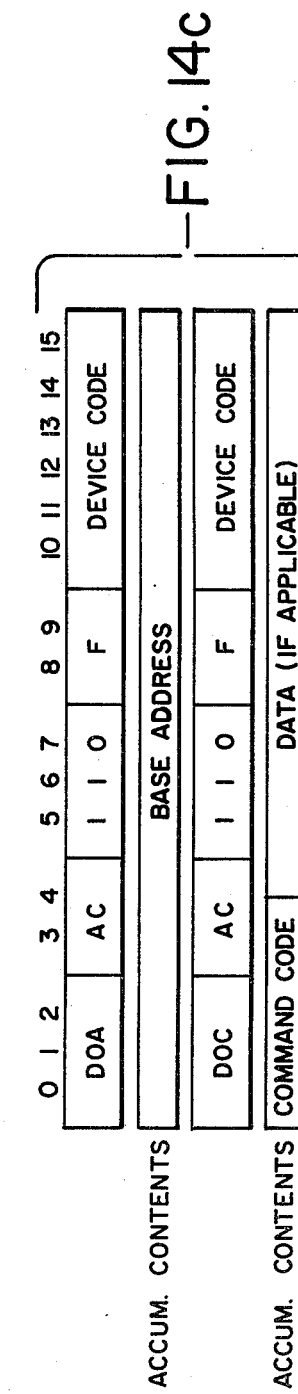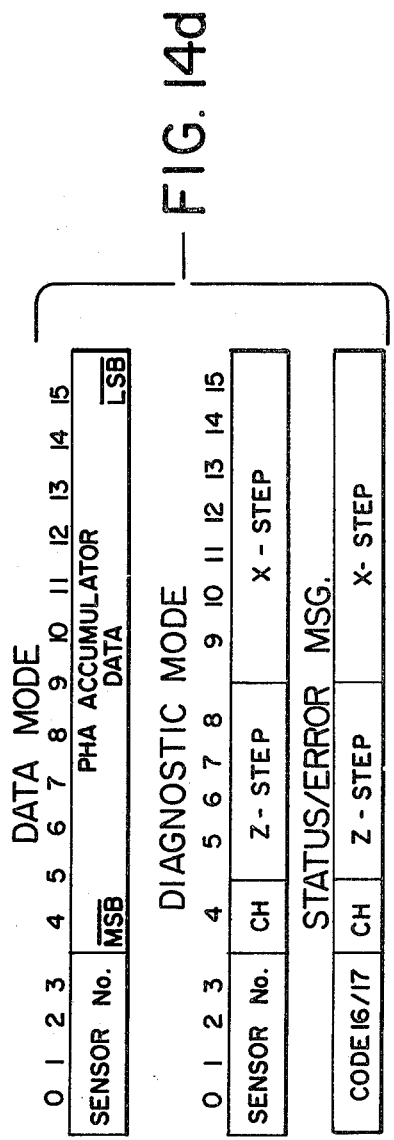

TRANSVERSE SECTION BRAIN IMAGER SCANNING MECHANISM

This invention relates to nuclear medicine. More particularly the present invention relates to an imager which very effectively enables the high sensitivity quantification and spatial location of the radioactivity of a body organ, such as the brain, of a patient who has been administered material tagged with radionuclides.

In the field of nuclear medicine, the importance of imaging has been recognized and the subject has been studied and investigated. See for example, "What is the Role of Nuclear Medicine in Medical Imaging" Edward M. Smith Sc.D., Maryville, Tenn.[*]; "Physics and Instrumentation"—Thomas F. Budinger and F. David Rollo "Progress in Cardiovascular Diseases, Vol. XX, No. 1 July/August 1977 pp 19-53; "Emission Computer Assisted Tomography with Single-Photon and Positron Annihilation Photon Emitters"—Thomas F. Budinger, Stephen E. Derenzo, Grant T. Gulberg, William L. Greenberg and Ronald H. Huesman.[**] Also, U.S. Pat. No. 3,970,853—David E. Kuhl and Roy Q. Edwards "Transverse Section Radionuclide Scanning System" has described a scanning system for obtaining in vivo transverse sections of the brain of a radionuclide administered patient. The scanning system in the Kuhl et al patent utilizes mildly focused collimators arranged in a rotating picture frame arrangement of offset interlaced radiation detectors. In the Kuhl et al system a "fat pencil" of sensitivity is utilized, and this system, while representing a significant contribution in the art of imaging, does not enable the desired optimal high degree of spatial resolution and sensitivity. Other techniques, utilizing "narrow pencils" of sensitivity, in order to improve spatial resolution, are even more hampered by what can be considered an imperative of nuclear medicine, i.e. the collection of a maximum amount of patient emitted radiation, e.g. gamma ray photons, during the short period of time which is compatible with patient immobility. Other efforts which employ gamma cameras and "parallel hole" collimators to simultaneously record many "narrow pencils" of radiation have been subject to similar difficulties.

[*] South Eastern Chapter, Society of Nuclear Medicine Continuing Education 1976.
[**] Journal of Computer Assisted Tomography Vol. 1, No. 1, 1977

It is accordingly an object of the present invention to provide a transverse section imager for use in nuclear medicine which rapidly collects emitted radiation from a transverse section of a body organ and enables a rapid, high-sensitivity quantification and spatial location of the radioactivity of the body organ in the transverse section.

Other objects will be apparent from the following description and claims taken in conjunction with the drawing wherein FIGS. 1 and 1(a) show the general arrangement of a particular embodiment of the present invention FIG. 2 shows, somewhat schematically, an imager in accordance with the present invention FIGS. 2(a), (b) and (c) illustrate a patient in relation to the imager of the present invention FIGS. 3, 3(a) and 3(b) show respectively a front, side and bottom view of a detector arrangement, including a highly focused collimator, for use in connection with the present invention FIG. 4 illustrates schematically an arrangement of highly focused collimators in accordance with the present invention and further illustrating representative relative movement of the collimators FIG. 4(a) and 4(b) illustrate schematically a scanning pattern of highly focused collimators in accordance with the present invention FIG. 5 shows a preferred scanning pattern in accordance with the present invention FIG. 5(a) and 5(b) illustrate particular representative portions of the scanning pattern of FIG. 5

FIG. 6 is a diagram used in connection with a mathematical presentation in the specification FIG. 7 schematically represents a general arrangement for the imager of the present invention FIG. 8 shows a display provided through the use of the present invention FIGS. 9(a)-9(f) and 10(a)-10(e) show various views of the preferred apparatus for the practice of the present invention FIG. 11 shows a general schematic for the transfer of data from the imager of the present invention to a general purpose computer FIGS. 11(a)-11(c) show timing diagrams related to FIG. 11

FIG. 11(d) shows a preferred embodiment of the scanner data multiplexer shown in FIG. 11

FIGS. 11(e) and 11(f) illustrate various components shown in FIGS. 11 to 11(d)

FIG. 12 schematically shows a portion of the device of FIG. 11(d)

FIG. 13 illustrates the loading of buffer storage in accordance with the device of FIG. 12

FIG. 14 shows command codes relevant to the device of FIG. 11(d)

Figure 2:
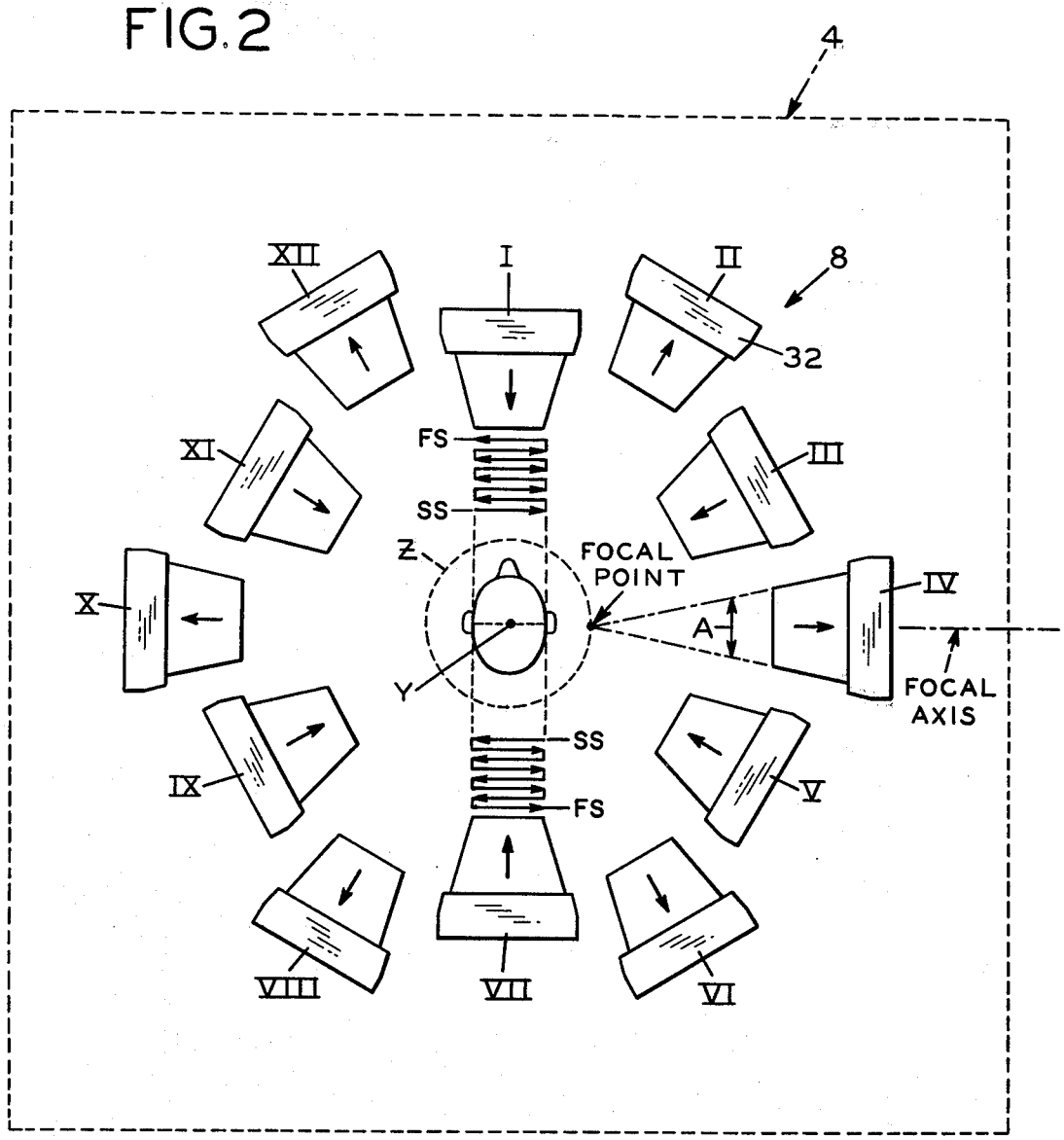

With reference to FIG. 1, a patient's couch is indicated at 1 which is provided with controls, not shown, for raising and lowering the couch 1, and for moving the headrest 3, of couch 1, in and out of the opening 5 of the gantry indicated at 4. Within gantry 4, as hereinafter more fully described, there is arranged, in a unique and novel manner, a plurality of scanning detectors, having highly focused collimators, from which electrical signals are obtained which are readily processed, e.g. by a general purpose computer, and enable a display at console 9 of a transverse section of the brain of a radionuclide administered patient, which display exhibits high sensitivity quantification and spatial resolution. The patient's couch 1 is moveable in and out of the opening 5 of the gantry 4 to provide for the scanning of a plurality of transverse sections.

With reference to FIG. 2, this figure shows at 8 an essentially schematic representation of the arrangement of scanning detectors within gantry 4. Each of the detectors indicated at I to XII in FIG. 2 is of a type more fully illustrated in FIGS. 3 and 3(a) which show a highly focused lead collimator at 30, a scintillation crystal at 32, a light pipe at 34 and a photomultiplier tube at 36. Such an arrangement suitably has the dimensions shown in the drawing when twelve detectors are used and suitably comprise a collimator made of antimony-bearing lead alloy containing a 22×26 array of tapered holes of rectangular cross-section. These holes are typically 0.320×0.160 in. on the face of the collimator that abuts the scintillation crystal 32, and about 60% of that size at the opposite face. All of the holes are convergent so that the axes intersect at a focus 6 inches from the collimator. The septa separating the holes are approximately 0.010 inch thick at the crystal face. A typical design resolution of collimator 30, defined as the full width between two points that give half amplitude for a point source of radiation is 0.3 inch in the plane of the transverse section and 0.5 inch perpendicular to the slice (slice thickness).

The scintillation crystal 32 typically comprises a thallium activated sodium iodide crystal mounted within a rectangular aluminum box and sealed under a window of ultraviolet transmitting glass. The bottom wall of the aluminum housing is thin, preferably less than 0.02 inches, to minimize absorption and scattering of the incident gamma rays.

A very important feature of the present invention is that the collimator used is highly focused at a single focal point, i.e. all the holes in the collimator converge at the focal point so that the collimator includes a large solid angle from about 0.05 to 1 steradian, preferably about 0.4 steradian, for collecting radiation.

In a configuration such as illustrated schematically in FIG. 2, where twelve focused collimators are used, the angle "A" is approximately and as close as practical to 30° (360÷12), e.g. about 24° and the angle "B" shown in FIGS. 2(b) and 3(a) is approximately 38.5°. When other than twelve collimators are used, e.g., 4, 8, 10, the design for angle "A" ($\pm 6°$) is obtained by dividing the number collimators into 360°. In the present invention, the focal length of the collimators (6 inches) is somewhat more than one-half the diameter of the scan field which surrounds the portion of the patients body which is scanned.

In the present invention, the preferred number of collimators is twelve to obtain high sensitivity and resolution in a short period of time, e.g., about 2 minutes per slice. The preferred range for the number of collimators is from 6 to 24 even numbers of collimators. Even numbers of collimators are preferred since they can be arranged in pairs with each collimator scanning half of the transverse section of the organ thereby minimizing effects of attenuation and scattering. With odd numbers of collimators, each collimator preferably scans the entire transverse section of the organ.

Figure 2A:
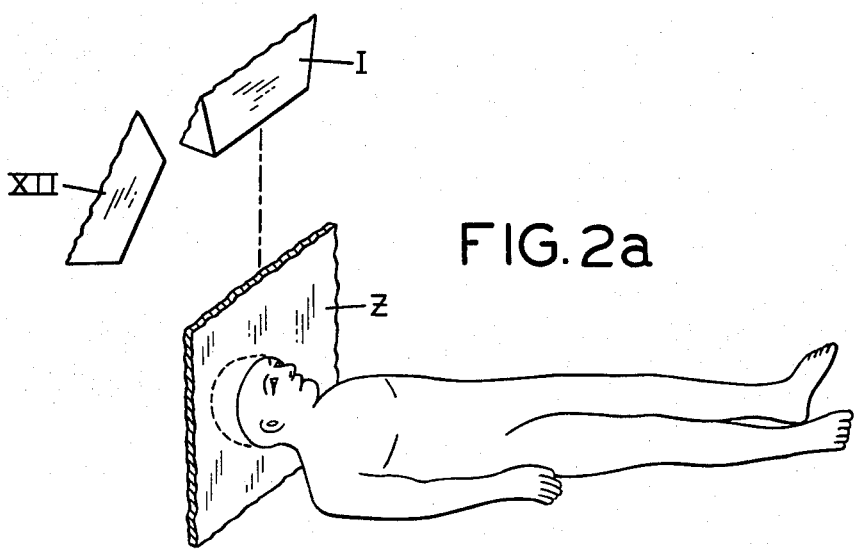

Referring again to FIG. 2, detectors I to XII are mechanically mounted and coupled in gantry 4, as hereinafter more fully described, to provide focal point scanning of a transverse section "Z" which is normal the head-to-toe axis of the patient and indicated schematically in FIG. 2(a). With reference to FIG. 2, which shows exemplary distances, the position of the detectors I–XII can be considered to represent the start (or finish) of a focal point scan. The alternate pairs of opposed detectors I–VII, III–IX, V–XI, are shown in what can be called the "full in" position. The other alternate pairs of opposed detectors II–VIII, IV–X, and VI–XII, are in what can be called the "full out" position. Upon commencement of a scan, each detector I–XII moves in a straight line tangential to the scan field Z in the same rotational sense (either clockwise or counter-clockwise angular rotation about the "head-to-toe" axis Y of the patient) the tangential travel of each detector being the same, a full diameter, or across two adjacent quadrants of scan field. Upon completion of each tangential travel, the "full in" detectors I, III, V, VII, IX and XI move away from the axis Y a predetermined increment normal to the tangential travel, the "full out" detectors "II, IV etc." move toward the axis Y by the same increment, and the direction of tangential travel of all detectors is reversed. This coordinated movement of the detectors is repeated until the focal point of each detector scans at least one half of the area of the scan field, preferably more than one-half as hereinafter described, at which time the scanning is completed and the initially "full in" detectors are in a "full out" position and vice versa. It is to be noted that the region scanned by the focal point of each detector overlaps, by an angular segment, the focal point scan of other detectors. In the case of twelve detectors, there is a 30° segment overlap of adjacent detectors and each scanned point in the scan field is scanned by the focal point of at least six detectors as hereinafter described.

Figure 5:
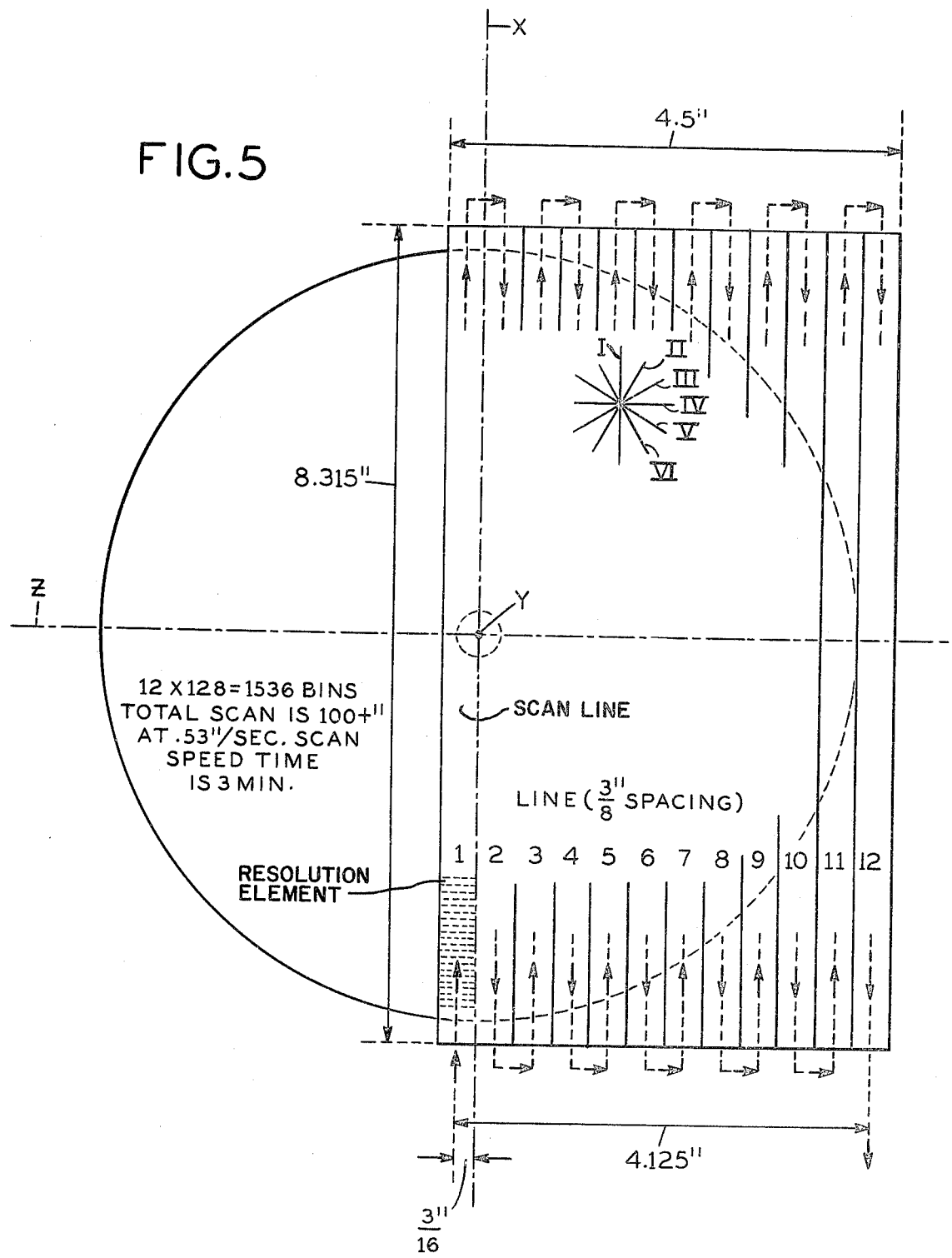
Figure 5A:
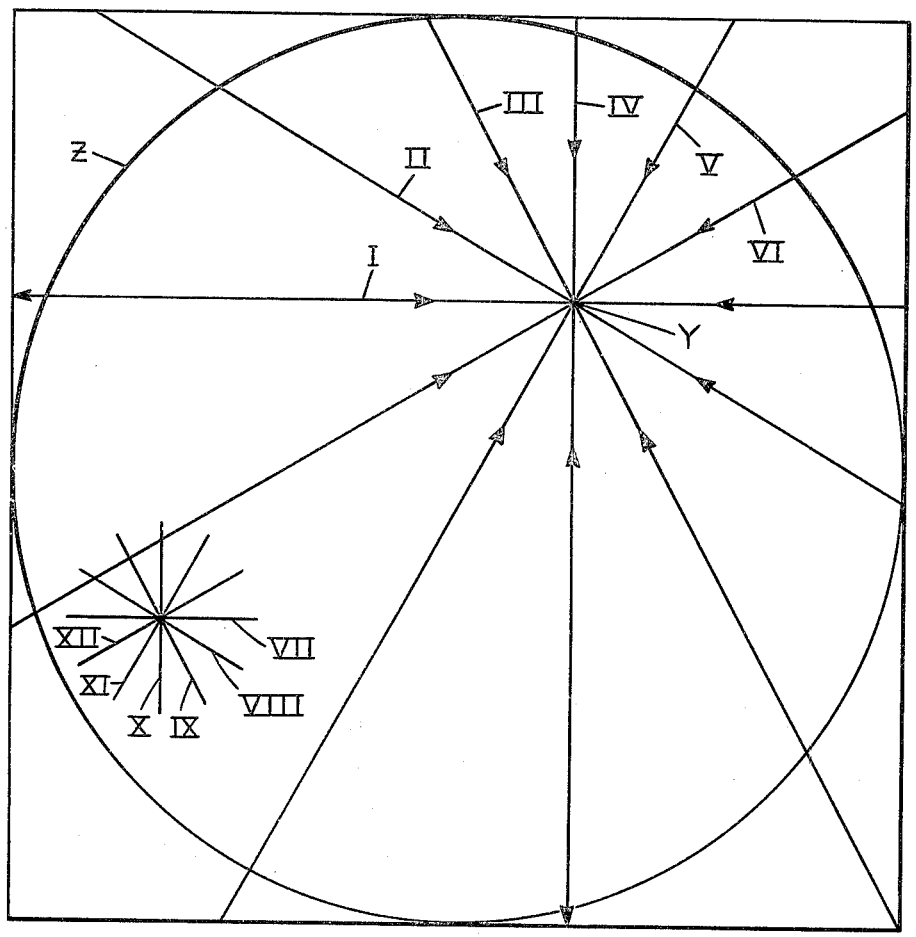
Figure 5B:
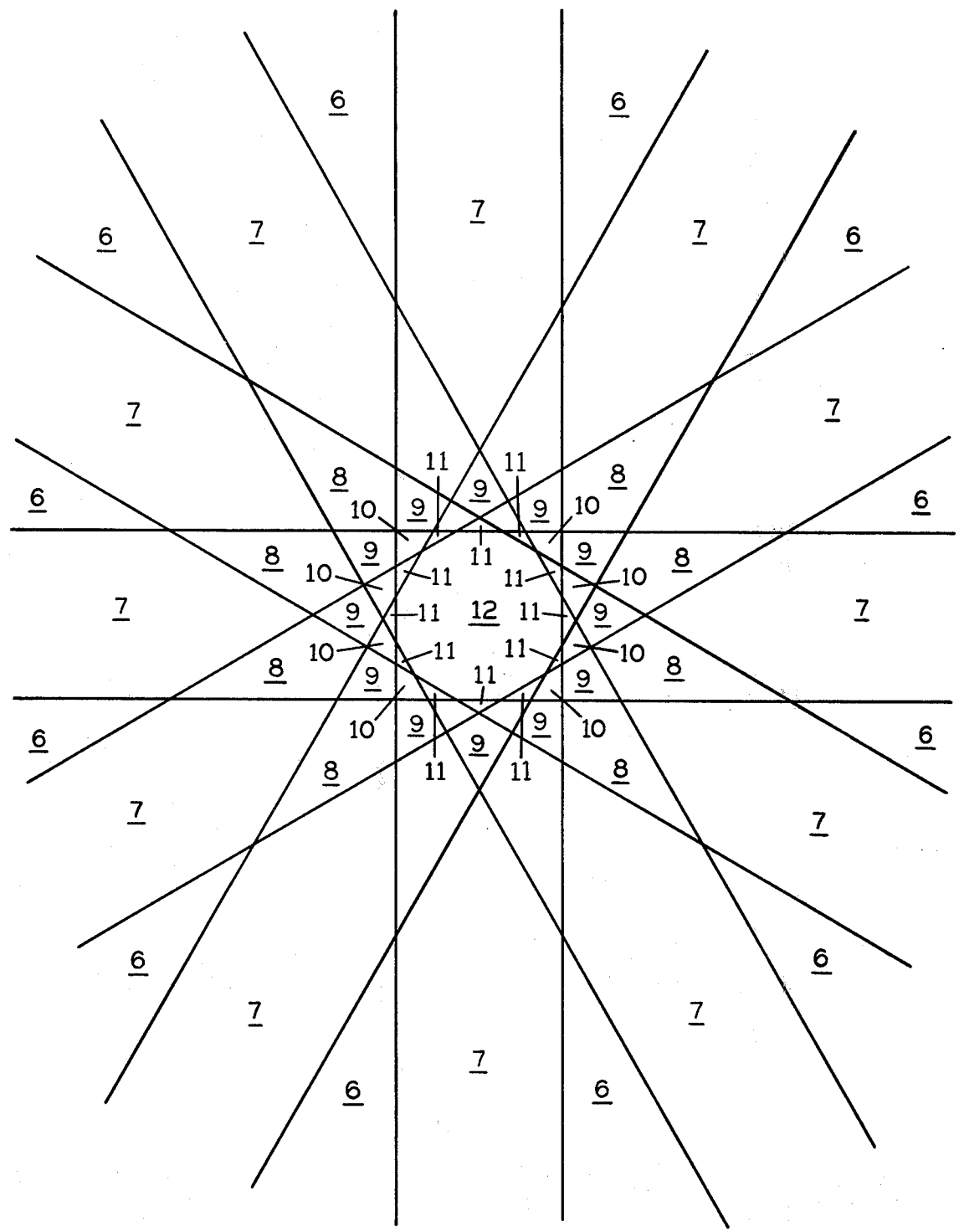

By way of further explanation, FIG. 4 shows schematically, the detectors I–XII at their respective halfway positions for calibration. FIG. 10(e) shows accurately the halfway position of the detectors in the preferred arrangement of FIG. 9. At the "½ way" positions shown in FIG. 4 all of the detectors I–XII are at the same distance from axis Y and as particularly illustrated for detector I, the focal point $FP_1$ is halfway in the scan field. As the scan is completed, detector I moved out and over following the tangential and incremental motion previously described, to the position I' where the focal point scan for detector I is completed (Full Scan I). Concurrently, the same relative motion is being experienced by detectors III, V, VII, IX and XI. The relative movement of the even numbered detectors is represented by detector II. As the scan is completed, detector II moves in and over to the position II' where the focal point scan for detector II is completed (Full Scan II). FIG. 4(a) illustrates schematically the focal point scan provided by each of the six "outward" moving detector I, III, etc. The scan shown is provided, for the respective detector, along the respective radial angle indicated, i.e. $a_I$, $a_{III}$–$a_{XI}$. A similar presentation is shown in FIG. 4(b) for the six "inward" going detectors II–XII. As is representatively illustrated in FIG. 5, any point in the transverse section Z is focal point scanned by at least one half of the total detectors, i.e., at least six in the presently considered embodiment. Because of overlaps the central region is scanned by up to 12 detectors. This overlap, which is provided by all twelve detectors in the preferred embodiment of the present invention, permits convenient equalization and normalization of the detectors. FIG. 5 shows a focal point scan for an "outward" going detector e.g. detector I and provides, for a twelve line scan, typical dimensions for scan line length (8.315 inches) spacing ⅜ inch), resolution elements (128 per line) and the like. As shown in FIG. 5, the exemplary point "R" is "focal point scanned" by the six detectors I, II, III, IV, V and VI. FIG. 5(a) is based on FIG. 5 and shows the detectors which scan two arbitrarily chosen points in the scan field which are scanned by six detectors; FIG. 5(b), also based on FIG. 5, shows the central region of the scan where scanning by up to twelve detectors occurs. The numbers in FIG. 5(b) show the number of detectors which scan the indicated region; the same type of information for any point in the scan field can be routinely determined from grids of this type in relation to the position of the detectors.

In the course of a transverse focal point scan as described above, each detector continuously receives the emitted radiation, e.g., gamma photons appearing within the included angle of the collimator and this radiation is converted into counts by the associated scintillation crystal and photomultiplier tube of each detector. Electrical signals provided by respective photomultiplier tube can be conventionally amplified, detected by pulse amplitude discrimination techniques, identified as to spatial orientation in the scan field and, in the form of digital numbers corresponding to counts and detector position, transferred to the memory of a general purpose computer. The stored information thus provided is, on account of using highly focused collimators in accordance with the present convention, readily reconstructed to provide a high sensitivty quantification and spatial location of the radioactivity in the transverse section which is focal point scanned. This is so since focussing collimators inherently sum the counts from each point, and by focal point scanning in and out as well as tangentially, the combination of collimators cover (sum) substantially 360° about each point in the transverse scan. The counts thus collected are predominantly counts originating at the focal points of the collimators but also include (convolved with) some counts from "out of focus points". These unwanted counts can be removed by deconvolving the stored information with a filter function $H(r)r^{-k}$ ($K>1$) by a relatively simple algorithm such as taking a Fourier transform of a ramp in frequency space; for example, as described in "The Fourier Reconstruction of a Head Section"—L. A. Shepp, B. F. Logan "IEEE Transactions on Nuclear Science" Vol. NS-21, June 1974. The resulting reconstructed data is then available for display showing quantified and spatially oriented radioactivity. Other known techniques can also be used to remove the unwanted counts.

The concept of using highly focused collimators for this purpose is based on the recognition that the Radon equation, can be put in a form that demonstrates that reconstruction using the counts summed (collected) over large angles is possible.

Figure 6:
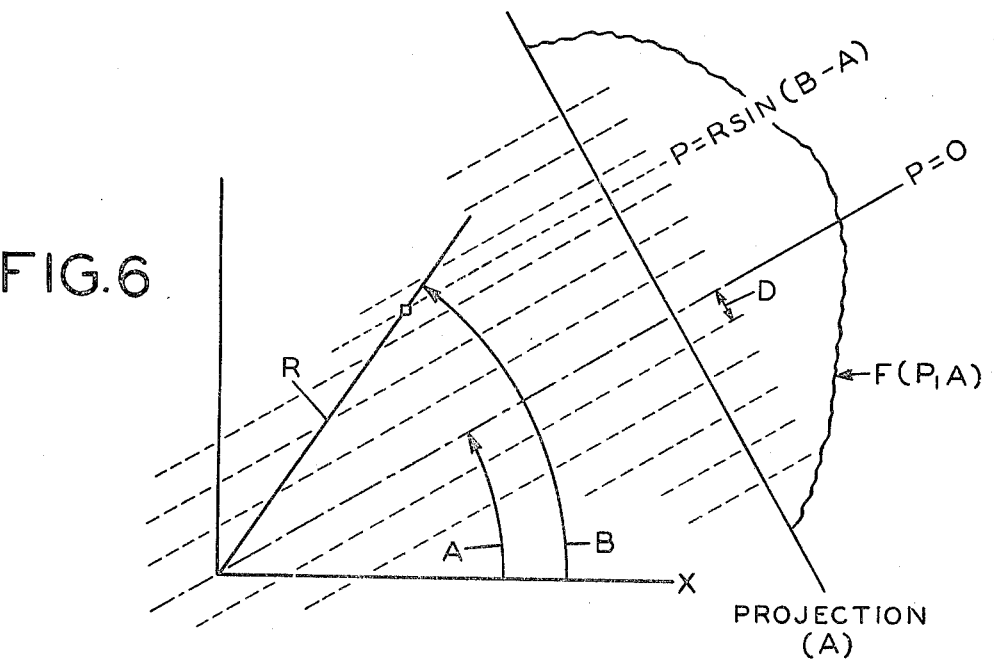

With reference to FIG. 6

RADON:

$$G(R,B) = \frac{1}{2\pi^2} \int_{-\pi/2}^{+\pi/2} \int_{-\infty}^{\infty} \frac{\partial F(,A)}{\partial P} \frac{1}{R \sin(B-A) - P} dP\, dA$$

$$= \frac{1}{2\pi^2} \int_0^{\pi} dA \int_{-\infty}^{\infty} \frac{dF(P,A)}{dP} \frac{1}{R \sin(B-A) - P} dP$$

To reconstruct a point at the origin:

$$G(o) = -\frac{1}{2\pi^2} \int_0^{\pi} dA \int_{-\infty}^{\infty} \frac{dF(P,A)}{P}$$

LET $dA = \Delta A$, $Am = m\Delta A$, $M$ = number of projections ($\pi/\Delta A$)

$dP = D$, $P = \eta D$

Replacing Derivative by Difference, $$G(o) = \frac{\Delta A}{2\pi^2} \sum_{m=1}^{M} \sum_{n=N}^{N} \frac{F[(n+1)D, m\Delta A] - F[nD, m\Delta A]}{\left(\frac{nD + (n+1)D}{2}\right)}$$

SINCE $\frac{\Delta A}{\pi} \sum_{m=1}^{M} F(m\Delta A) = \overline{F}(\ )$ The average of $F(\ )$ over all angles AND $\frac{nD + (n+1)D}{2} = \frac{D}{2}(2n+1)$ $$G(o) = -\frac{1}{2\pi} \cdot \frac{2}{D} \sum_{n=-N}^{N} \frac{\overline{F}[(n+1)D] - \overline{F}(nD)}{2n+1}$$

-continued $$= -\frac{1}{D\pi} \left\{ \frac{\overline{F}(D) - \overline{F}(o)}{1} + \frac{\overline{F}(2D) - \overline{F}(D)}{3} + \right.$$
$$(n = o) \qquad (n = 1)$$

$$\left. \frac{\overline{F}(o) - \overline{F}(-D)}{-1} + \ldots \right\}$$
$$(n = -1)(n = 2)(n = -2)$$

$$= \frac{1}{D\pi} \left\{ \overline{F}(o) + \frac{1}{3} [\overline{F}(D) + \overline{F}(-D)] + \right.$$

$$\left. \frac{1}{15} [\overline{F}(2D) + \overline{F}(-2D)] + \ldots \right\}$$

$$G(o) =$$

$$\frac{4}{D\pi} \left\{ \frac{\overline{F}(o)}{2} - \sum_{n=1}^{N} \frac{\overline{F}(nD)}{(4n^2 - 1)} - \sum_{n=-N}^{-1} \frac{\overline{F}(nD)}{(4n^2 - 1)} \right\}$$

In the final equation above $\overline{F}(o)$, $\overline{F}(nD)$ are directly measured by the collimators and associated detectors.

With reference to FIG. 7, and the previous description, each focal point scan line of each detector I–XII, is divided uniformly into 128 discrete resolution elements, the location of which in the scan field is derived routinely from the mechanism of the gantry scan drive hereinafter more fully described. As a detector passes through the resolution elements of a scan line and uniformly samples the resolution elements, accumulator 810 accumulates counts from the detector photomultipliers for the time of detector travel through each resolution element. For example, for a typical resolution element travel time of 150 milliseconds, the accumulator will receive the counts developed by the detector photomultiplier during $4.8\mu$ second intervals which have an acceptable pulse amplitude as established by a pulse amplitude discrimator circuit in combination with an associated detector. When the counts for a given resolution element have been received by the accumulator 810, this data is transferred to general purpose computer 840 for storage at an address corresponding to the spatial location, i.e. a grid is established in which, for each resolution element in the grid, the corresponding count data representing a quantification of collected counts is stored.

Figure 8:
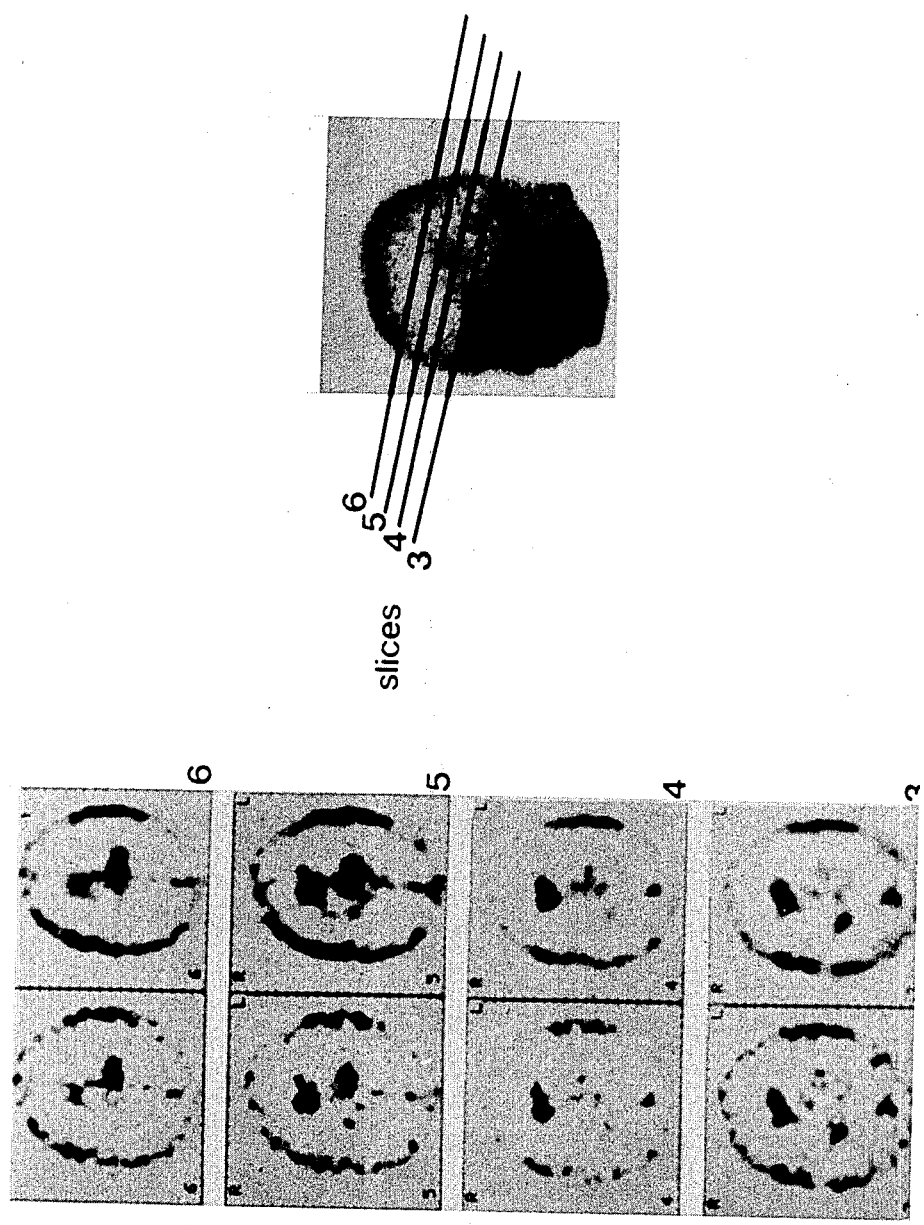

The stored data is then processed by an algorithm, preferably as described above, which provides data for display as exemplified in FIG. 8.

In the preferred embodiment of the present invention involving 12 scan lines per detector with 128 resolution elements per line, the scintillation count data from all of the detectors, involving 12 scan lines per detector with 128 resolution elements, per line, is stored at contiguous memory locations with the scan line data for each pair of opposed detectors being stored at contiguous memory locations in a manner which makes it appear that the opposing detectors travel in the same direction, as hereinafter described. This compensates for the opposite travel of opposed detectors. Each scan line is processed by the computer under program control deconvolving the stored information as previously described; since each opposing detector scans 12 lines, but 2 of these lines overlap, as previously mentioned, a merged $22 \times 128$ array is produced, one for each detector pair. The merged arrays are then summed into one $128 \times 128$ array taking into account the angular (30°) orientation of each array. The result is stored and is available to make a picture display.

Figure 9E:
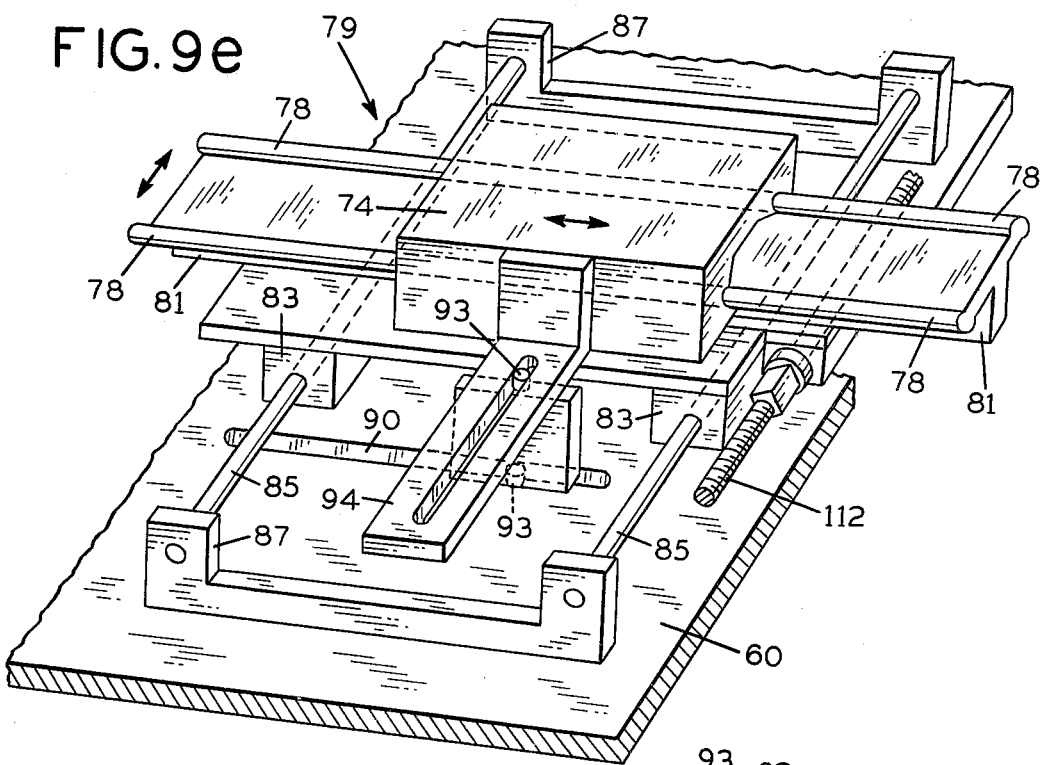
Figure 9D:
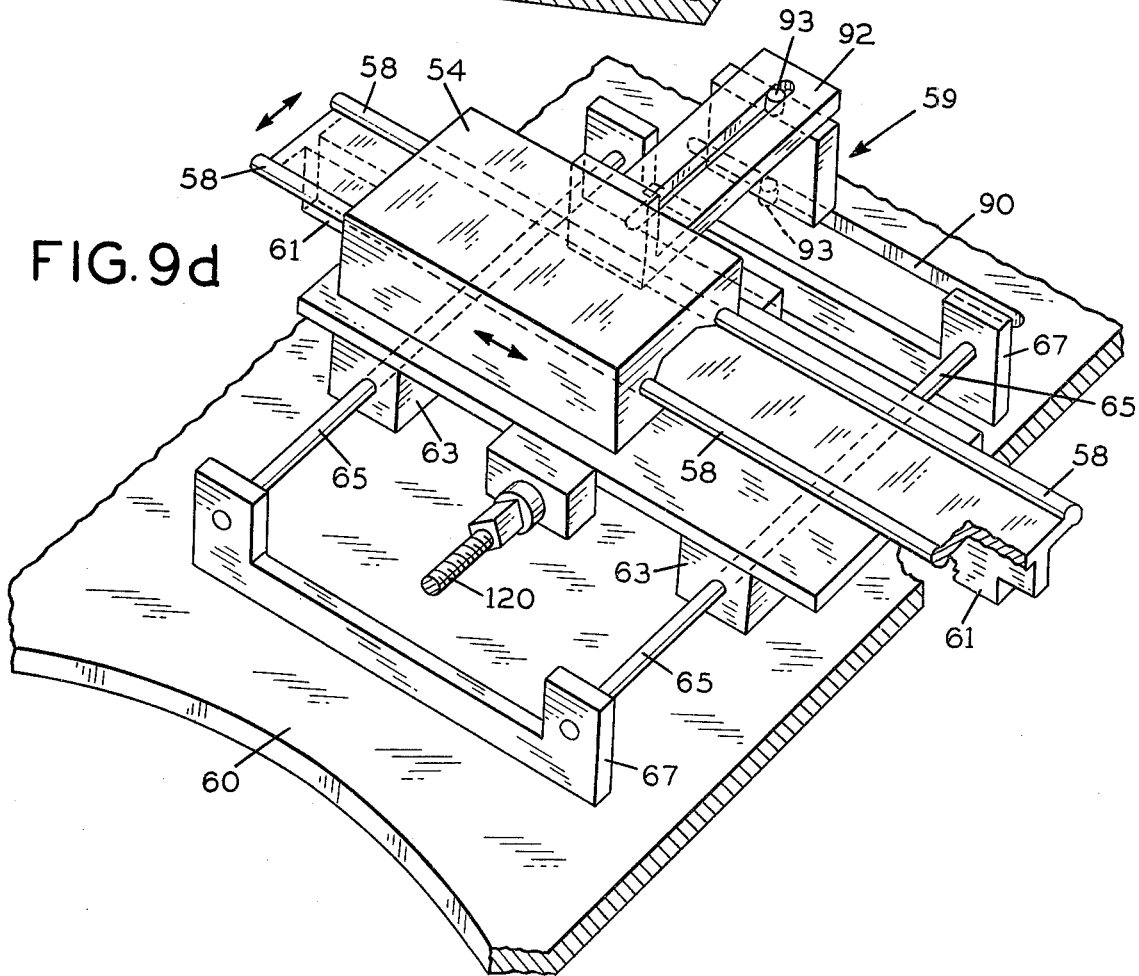

With reference to FIGS. 9(a)–9(e) these Figures show, in conjunction with FIGS. 10(a)–10(e), a novel and preferred means for providing the 360° focal point scanning hereinabove described. FIG. 9(a) is an assembly view showing a gantry 4 to which is attached a vertical main plate, 60, suitably of ⅜ in. aluminum ribbed casting. Attached to the rear side of main plate 60 is a rotably mounted disk 260 having a slotted arm 250, shown more clearly in FIG. 10(c), which engages a cam follower 240 which travels in tangential slot 245 according to the movement of drive block 220 shown more clearly in FIG. 9(a). Directly below tangential slot 245 is a shorter tangential slot 90, with identical tangential slots 90 located on the same radius at 30° intervals. Alternate assemblies, indicated at 59, are arranged radially inward from adjacent slots 90 and the alternate tracking assemblies indicated at 79 are arranged radially outward from adjacent slots 90. With reference to FIG. 10(d), channel supports 50 are fixedly engaged to tracking assemblies 59, and support detector assemblies I, III, V, VII, IX and XI which are held in place at 52; channel supports 70 are fixed engaged to tracking assemblies 79, and support detector assemblies II, IV, VI, VIII, X and XII which are held in place at 72. In operation, a first stepping motor 200, through coupled screw 210 and arm 250 of disk 260, drives the tracking assemblies 59, 79, in the same (i.e., either clockwise, or counter clockwise) tangential direction for a distance equal to a scan line (shown in FIG. 10(c); upon completion of a scan line, stepping motor 118 mounted on the back of plate 60, through belt drive 119 and coupled screw 112, moves a single tracking assembly 79 (in FIG. 9(a) this is the tracking assembly for detector X) in a direction transverse to tangential slot 90, an increment corresponding to the desired distance between scan lines. When the incremental movement is inward, bevel gear 110 for detector X drives the engaged oppositely rotatable bevel gears 100 to move the engaged tracking assemblies 59 outward the same amount of incremental movement. Thus alternate detectors scan "in" while the adjacent detector scan "out" and vice versa. Further in regard to FIG. 9(a), this view shows an assembly view of the scanning means with the illustrating twelve detectors numbered I–XII, as before, shown in the "halfway" calibration position of FIG. 4. The detectors I–XII have collimators 30 wherein the angle "A" is as close as practical to 360°÷12=30°, e.g., about 24°, to permit a minimum clearance between adjacent scintillation crystals 32, which in FIG. 9(a), are shown slightly beveled at 33 to permit an optimally close fit.

Alternate detectors I, III, V–XI, with their associated collimators 30, scintillation crystals 32, light pipes 34 and photomultipliers 26 are mounted on channel supports 50 at 52 as previously mentioned; supports 50 are fixedly mounted to carriages 54 as shown at 56 in FIG. 9(b). Carriages 54 are part of a tracking assembly 59, illustrated in FIG. 9(d) which includes rails 58 fixed to amount 61, shown in FIGS. 9(b) and 9(d) along which carriages 54 travel during the scanning operation as hereinafter described. Rails 65 are fixedly mounted to main plate 60 by supports 67, with rails 65 aligned normal to an adjacent slot 90 and centrally aligned therewith.

The other alternate detectors, II, IV–XII, with their associated collimators 30, scintillator crystals 32, light pipes 34 and photomultipliers 36 are mounted on channel supports 70 at 52 as previously mentioned; supports 70 are fixedly mounted to carriages 74 as shown at 57 in FIG. 9(c). Carriages 74 are part of a tracking assembly 79, illustrated in FIG. 9(e), which includes rails 78 fixed to a mount 81, shown in FIGS. 9(c) and 9(e) along which carriages 74 travel during the scanning operation as hereinafter described. Mount 81 is fixed to slide 83 which moves along rails 85 parallel to a tangential slot 90 during the scanning operation as hereinafter described. Rails 85 are aligned normal to an adjacent slot 90 and centrally aligned therewith. The rails 85 and 65 are located on mounts which are at a common distance away from slot 90. Tracking assemblies 59, and 79, as thus far described, are identical but are located, alternatively on opposite sides of their adjacent tangential slots 90 in main plate 60. Tracking assemblies 59 have outward extending slotted brackets 92, connected to carriages 54, which engage a cam follower 93 which travels on block 91 in its associated slot 90.

Tracking assemblies 79 have inward extending slotted brackets 94, connected to carriages 74, which engage a cam follower 95 on block 96 which travels in its associated slot 90. The movement of the slotted brackets 92 and 94, by the action of cam followers 93 and 95, as noted above, and hereinafter more completely described, results in tangential scanning movement of the detectors I–XII. The alternative "in" and "out" scanning movement of detectors I–XII is, as noted above, and hereinafter more completely described, derived from bevel gears 100, which are engaged to tracking assemblies 59, and oppositely rotating bevel gears 110, which are engaged to tracking assemblies 79 as can be seen more clearly in FIG. 9(f). With reference to FIG. 9(f) the tracking assembly 79 for detector X is shown coupled to its bevel gear 110 by way of coupled screw 112 and gear-belt arrangement 114 and bevel gear shaft 116. Coupled screw 112 is driven by stepping motor 118, driving the tracking assembly 79 for detector X "in" or "out", depending on the direction of stepping motor 118, and also turning bevel gear 110; this is the only bevel gear directly driven. The adjacent bevel gears 100 are driven by bevel gear 110 in the direction opposite to gear 110 and coupled screw 120, engaged to bevel gear 100 moves tracking assembly 59 "out" when assembly 79 is moving "in" and vice versa. As a result, all the tracking assemblies "79" move "in" together, while tracking assemblies 59 move "out" together, and vice versa.

Figure 10A:
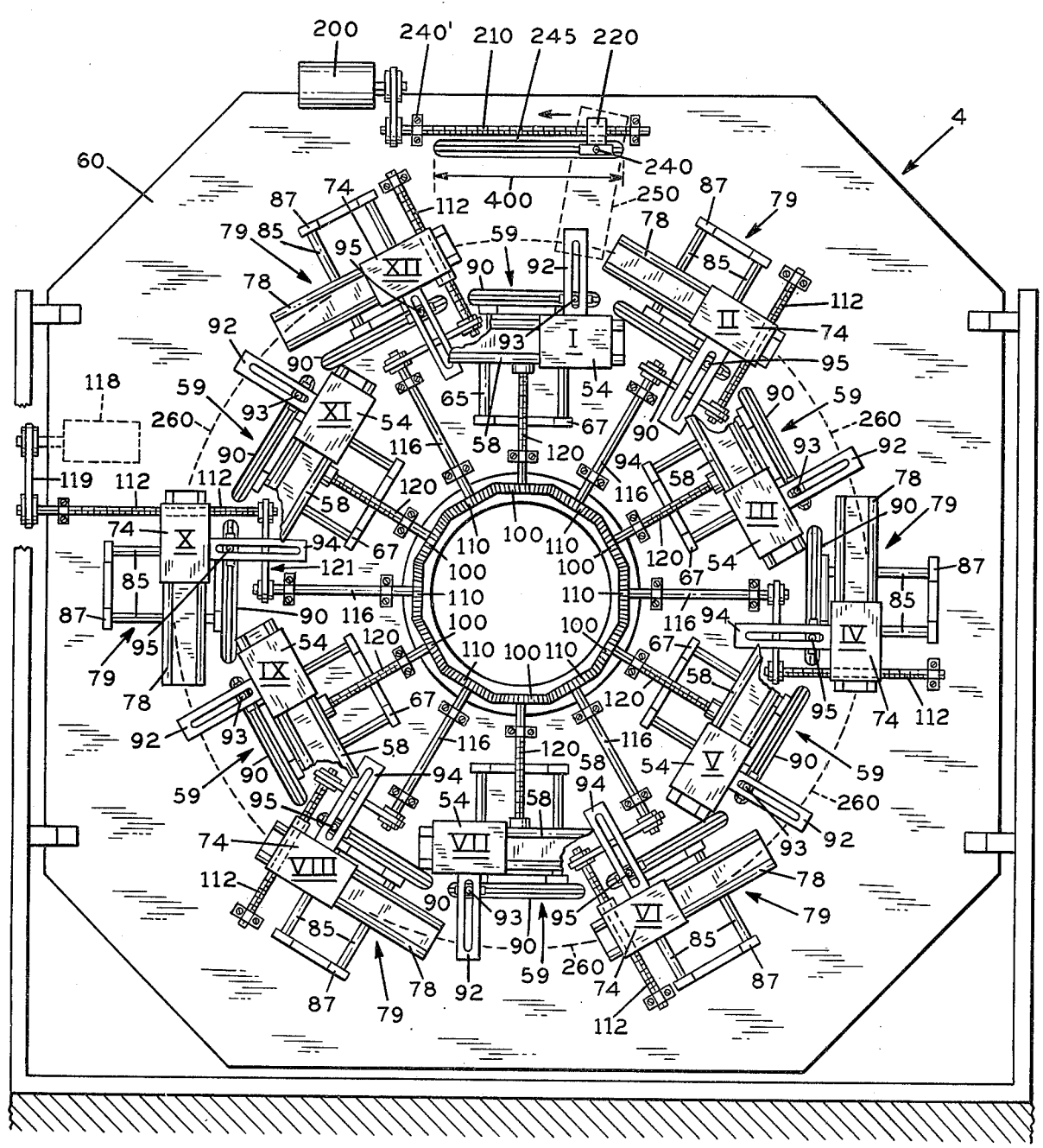
Figure 10C:
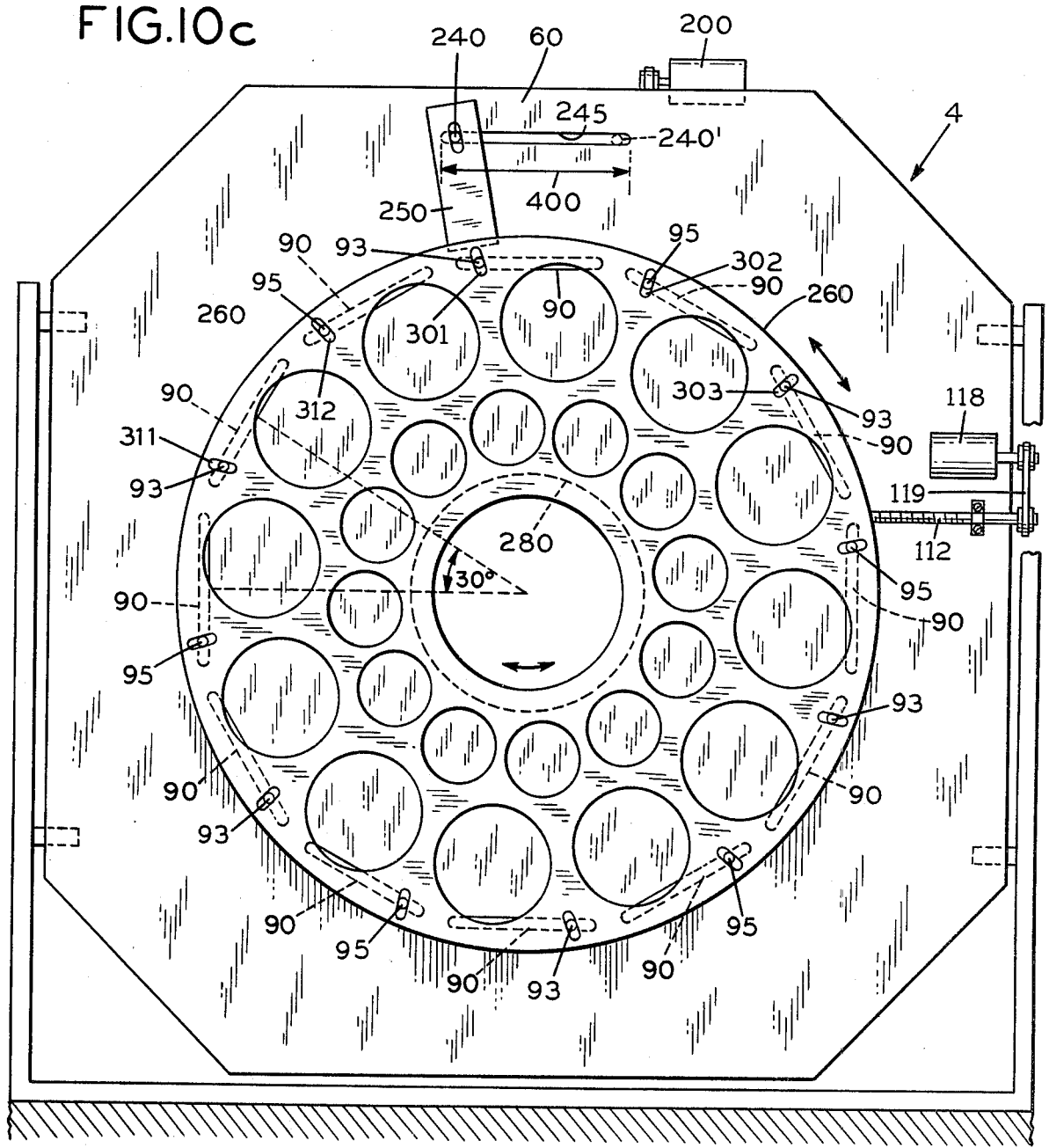
Figure 10B:
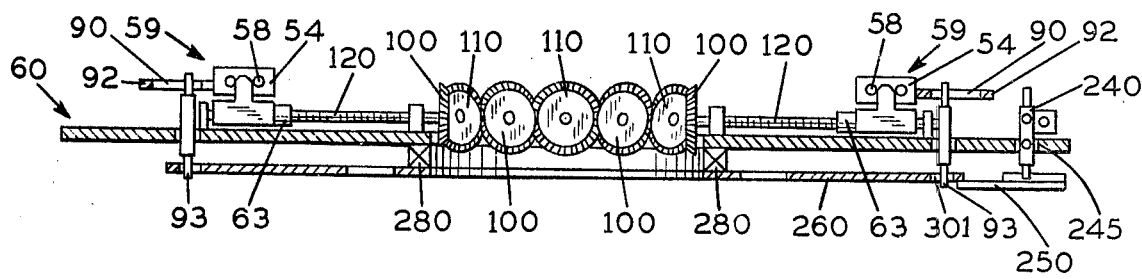
Figure 10D:
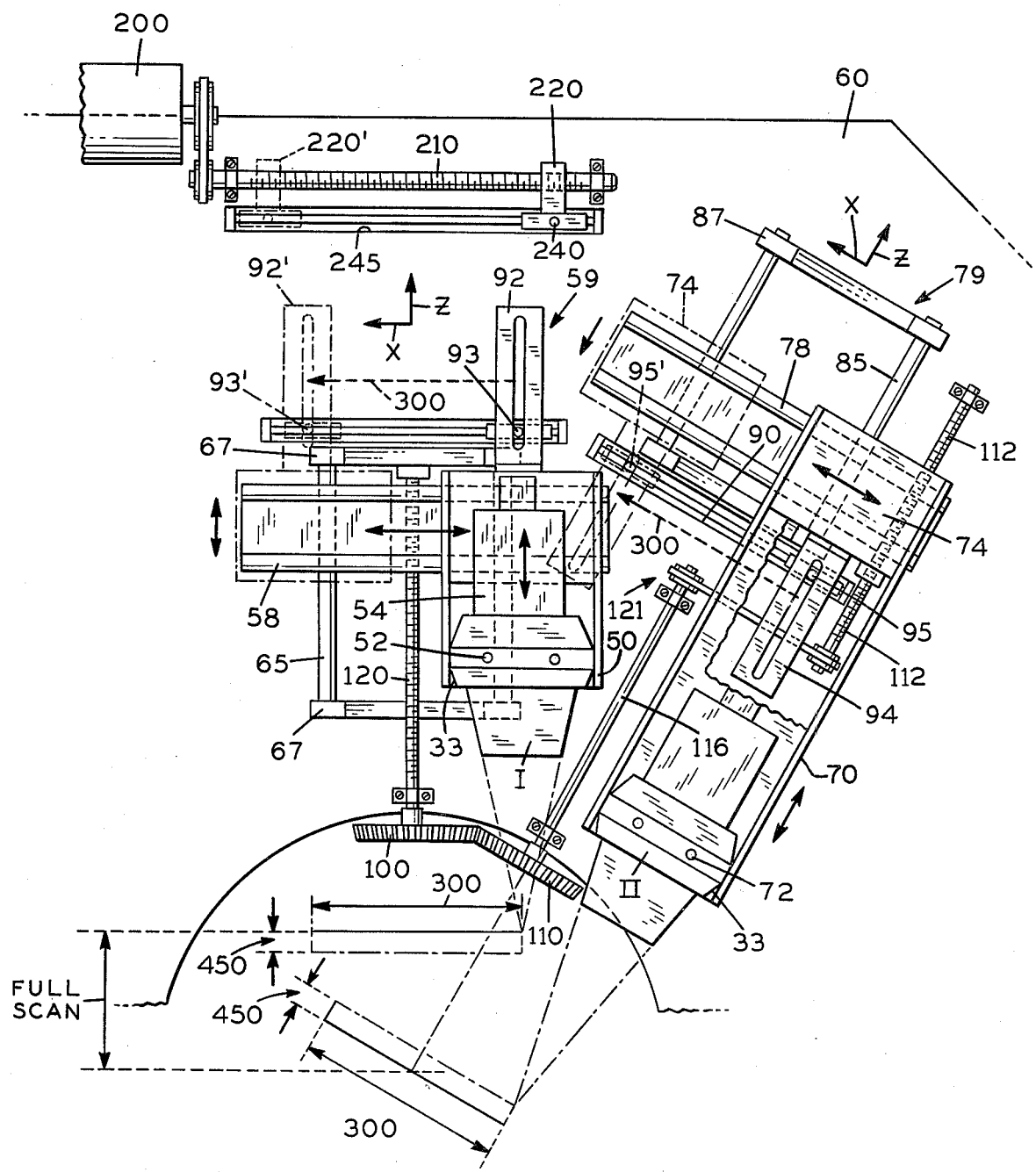
Figure 10E:
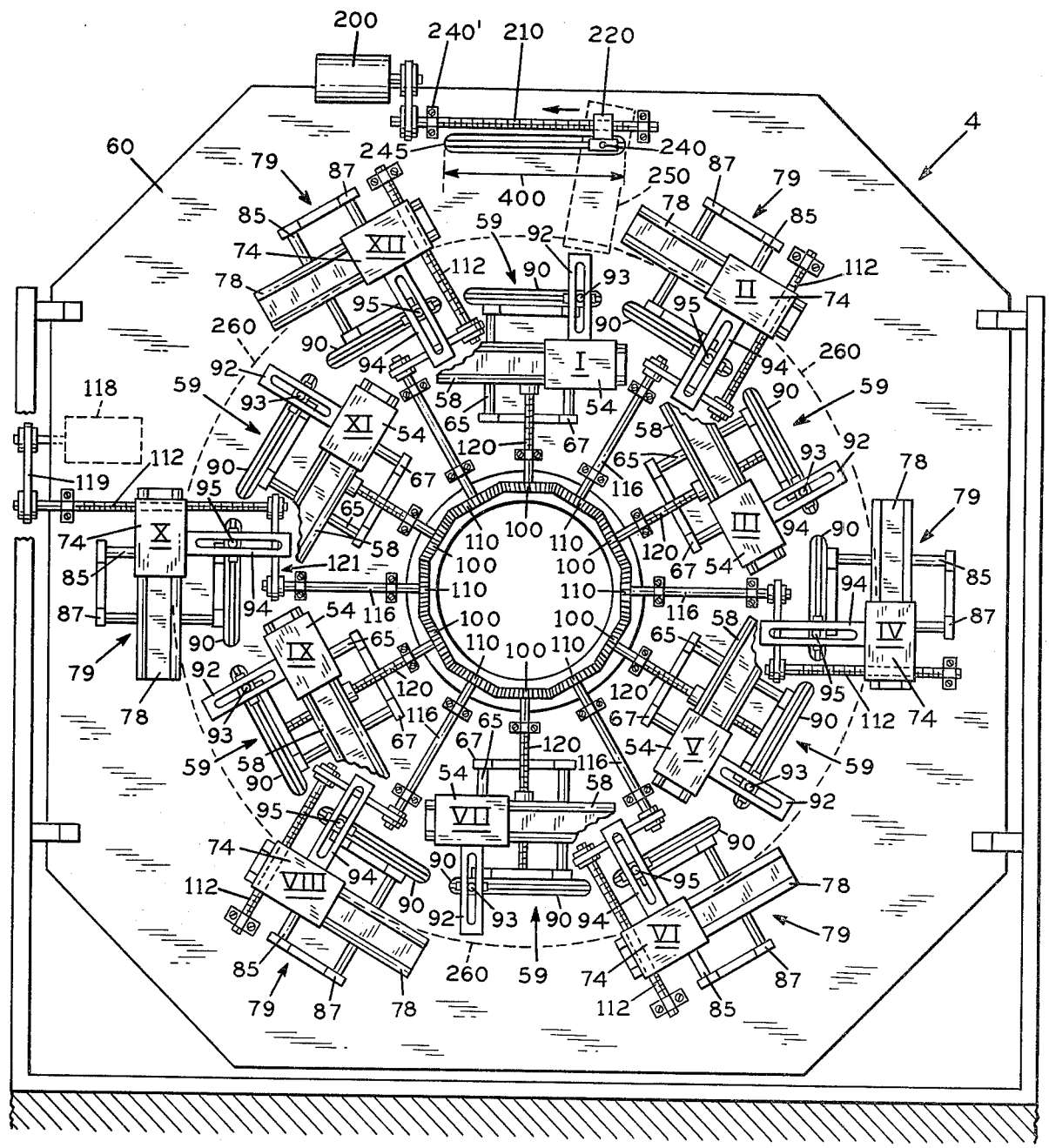

With reference to FIG. 10(a), this view shows the apparatus of FIG. 9(a) with the detectors and support channels removed. FIG. 10 (b) shows a side elevation in section of FIG. 10(a) and FIG. 10(c) shows a back view of FIG. 10(a). In FIG. 10(a ) tracking assemblies 59 are in "full out" position, and tracking assemblies 79 are in "full in" position, representing the start of a scan. It is to be noted that FIG. 9(a) represents a "½ way" scan position for all the tracking assemblies which is used for calibration, FIG. 10(a)–10(c) represent an "in", "out" condition. The true "½ way" scan position is illustrated in FIG. 10(e). In FIG. 10(a), at the start of a scanning operation, stepping motor 200, mounted on the front of plate 60 drives coupled screw 210 which causes engaged drive block 220 to move along rail 230 in the direction indicated. The drive block 220 is fixed to a cam follower 240 which passes through tangential slot 245 in plate 60. As shown in FIGS. 10(b) and 10(c), a slotted arm 250 is mounted on a rotating disk 260 which is rotatably mounted in bearings 280 on the reverse side of plate 60. Disk 260 has a slot 301 directly below the slotted arm 250, and slots 302≅312, at 30° angular intervals. Each of these slots 301–312 engage a cam follower 93 in slot 90 which engages the bracket member 92 of a tracking assembly 59, or a cam follower 95 which engages the bracket member 94 of a tracking assembly 79. Thus, considering the position of tracking assemblies 59 and 79 in FIG. 10(a) to represent the beginning of a scan, with representative detector positions as shown in FIG. 10(d), stepping motor 200 is energized to drive coupled screw 210 whereby drive block 220 moves tangentially to the left in slot 245 a distance of 11.2 inches shown at 400 in FIG. 10 (c). This distance of travel for drive block 22, and cam follower 240 is such that cam followers 93 and 95 in tangential slots 90 all move at the same time a counter-clockwise tangential distance 300 equal to a scan line as shown in FIG. 5 and FIG. 10(d), with a predetermined number of steps of travel being a scanning resolution element, as hereinabove described, typically 1/128 of the scan line distance 300. When the tangential carriage movement travel of 300 of the carriages 54 and 74 along rails 58 and 78 has been completed, a signal is provided, e.g., from a general purpose computer, or otherwise, which actuates stepping motor 118, which is engaged to coupled screw 112 by belt 119, and to the shaft 116 of bevel gear 110 by belt drive coupling 121. Bracket members 94 have clearance to pass under rails 58 can be seen from FIG. 9(e). The above-described linkage is arranged such that a number of steps of motor 118 causes coupled screw 112 to move slide 83 of the indicated tracking assembly 79 outward, and also carriage 74, a distance equal to the desired scan line separation shown as 450 in FIG. 10(d). Concurrently the adjacent bevel gear 100, as shown in FIG. 9(f) rotate oppositely to bevel gear 110, while the other bevel gears 110 for detectors II, IV, etc., rotate in the same direction as the motor driven bevel gear 110 for detector X. Consequently, when the carriage 74 for a detector X (II, IV, VI, etc.) moves outward a scan line separation distance 450, the carriages 54 for detectors I, III,–XI move inward a scan line distance 450 can be seen from FIG. 9(f) for the carriage of detector XI. The rotation of bevel gear 100, oppositely to bevel gear 110, causes coupled screw 120 to move slide 63, and hence carriage 54 inward while carriage 74 moves outward. At this time, an appropriate signal to stepping motor 200 causes coupled screw 210 to rotate opposite to its first direction and tangential travel of block 220 and cam followers 93 and 95 occurs as before, but now in the opposite a clockwise direction. A second scan line is provided for all of the detectors I–XII and stepping motor 118 is re-actuated and the inward and outward movement of the detectors, as previously described, is repeated. This cycle of operation is continued until a "Full Scan" indicated in FIG. 10(d) is completed.

In the apparatus of the present invention described above the scan line direction is explained as a movement of a tracking assembly, tangential to the scan area in the center of the apparatus. The prime mover for the scan line motion, is a single stepping motor which turns a screw which moves a drive block tangentially along a set of rails. The drive block is connected by a cam follower to a slotted arm attached to a rotatable disk. The disk is connected to the main mounting plate by a large ball bearing which allows the disc to rotate when driven by the drive block. Each of the tracking assemblies are connected by connecting blocks, having cam followers on each end, to slots in the disc. These connecting blocks convert the rotary motion of the disk to linear motion of the tracking assemblies. Since all the connecting blocks are located on the same radius of the mounting plate, the motion of all the tracking assemblies are synchronized, and the speed and location of the tracking assemblies are proportional to the speed and location of the drive block. The "in-out" direction is the radial motion of a tracking assembly with respect to the circular scan area. When a scan-line movement has been completed, that is, when the carriages on the tracking assemblies have moved from one extreme position to the opposing extreme position, the "in-out" prime mover, a second stepping motor, turns a screw which moves one outer tracking assembly some unit distance away from the center of the scan area. The screw that moves that one outer tracking assembly is connected to a shaft by a positive drive belt. On the end of this shaft, towards the center, is mounted a bevel gear—in the drawing a 30° bevel gear. This bevel gear drives eleven other 30° bevel gears which form a complete circle. The two bevel gears on either side of the drive bevel gear will rotate in the opposite direction of the drive bevel gear. The bevel gears other than the driven bevel gear, are attached to drive screws which drive attached inner tracking assemblies. The tracking assemblies driven off the bevel gear, shaft, positive drive belt, screw combination are outer tracking assemblies. In this case, there are six of each alternately spaced around the scan area. When the "in-out" prime mover causes the far left outer tracking assembly to move outward one unit of distance, the bevel gear assembly causes all the inner tracking assemblies to move inward one unit of distance and at the same time causes the other five outer tracking assemblies to move outward one unit of distance. To allow for this inward and outward motion of the tracking assemblies and still maintain the proper connection between the connecting block and the carriages a slotted bracket is rigidly mounted to each carriage. The cam follower on the end of the connecting block transfers the tangential motion to the carriages. Since all the movements of the tracking assemblies are mechanically connected together and controlled by only one prime mover for each direction, there is no possible error in electronic signal or component failure that could cause any of the detectors, mounted and moved by the tracking assemblies, to collide with one another. The unique movement in the "in-out" direction of the outer tracking assemblies moving outward while the inner tracking assemblies move inward allows for the tightest possible packaging of the detectors. More important, it allows for the shortest possible focal distance for the detector collimators, and the angular spacing of about 30° between the collimators remains constant throughout the scanning operation.

Figure 11:
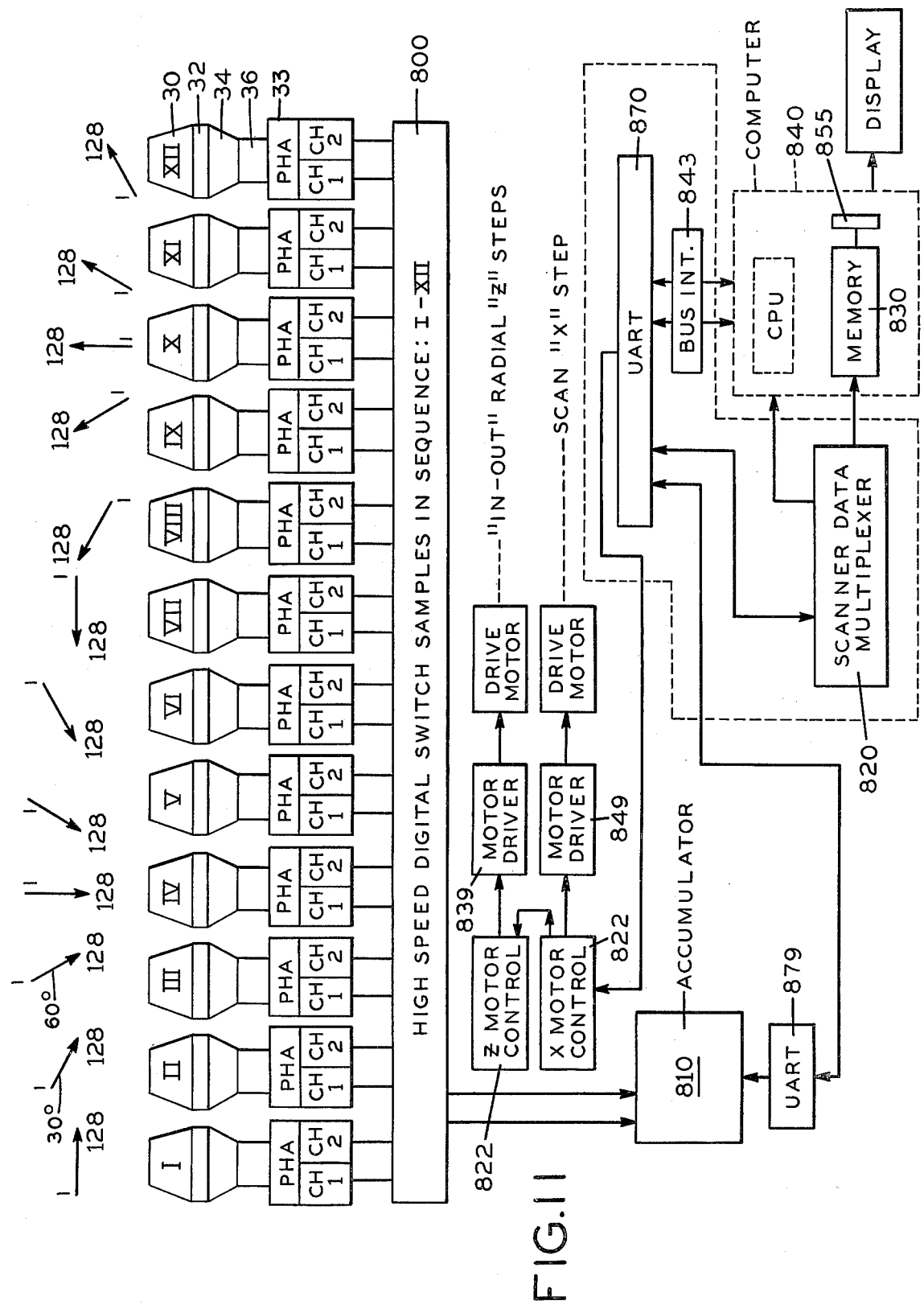
Figure 11A:
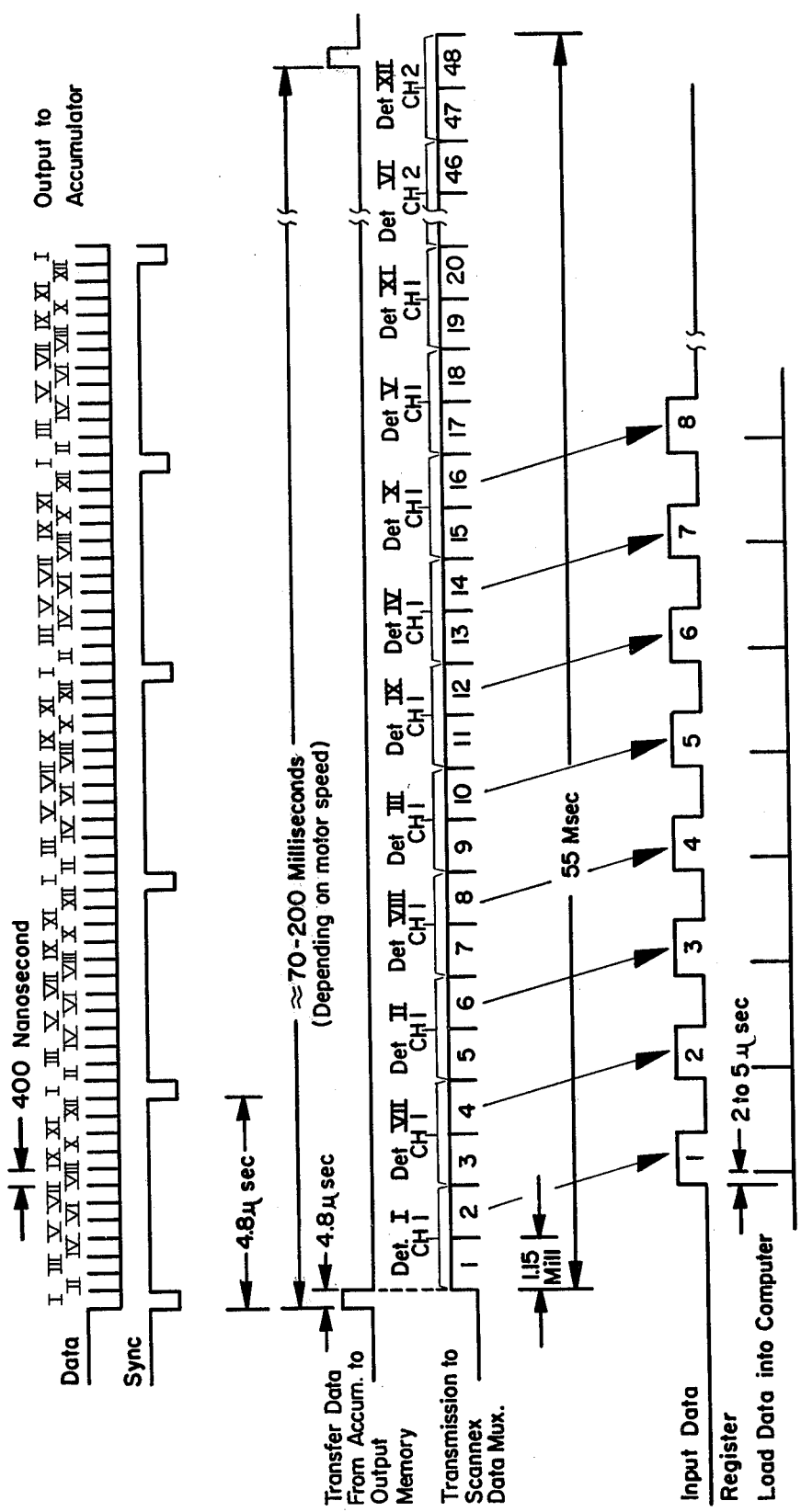
Figure 11B:
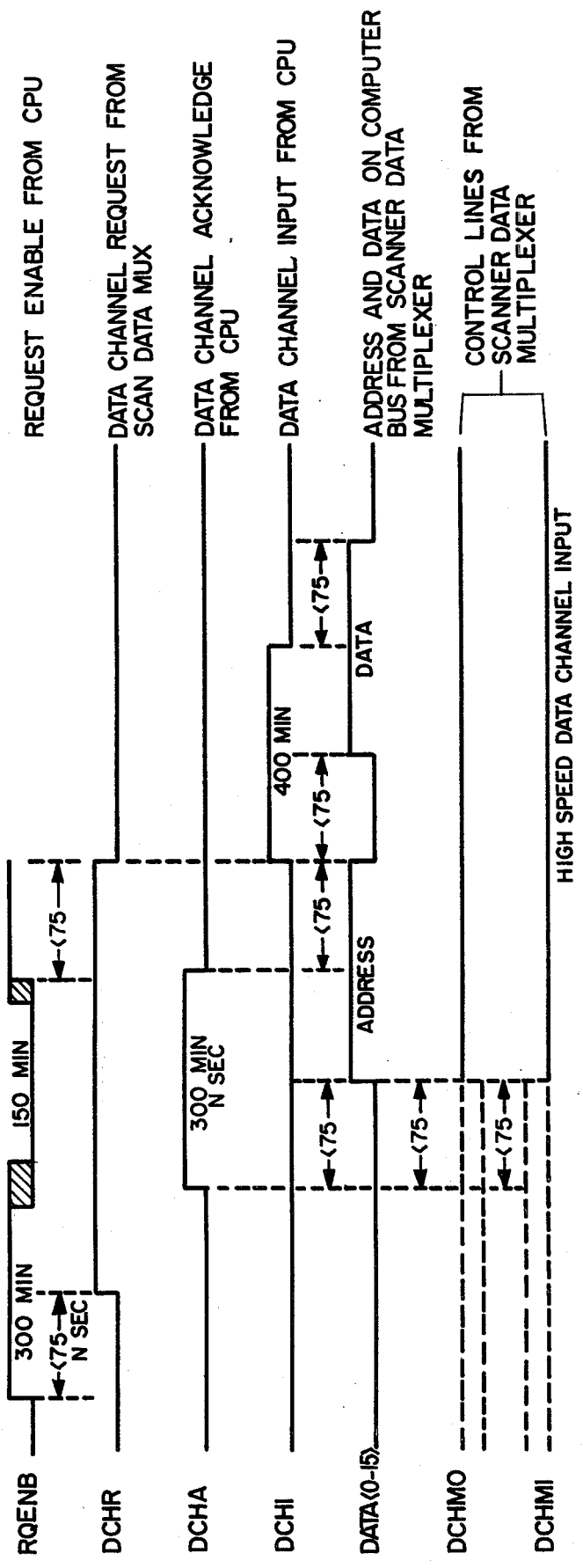
Figure 11C:
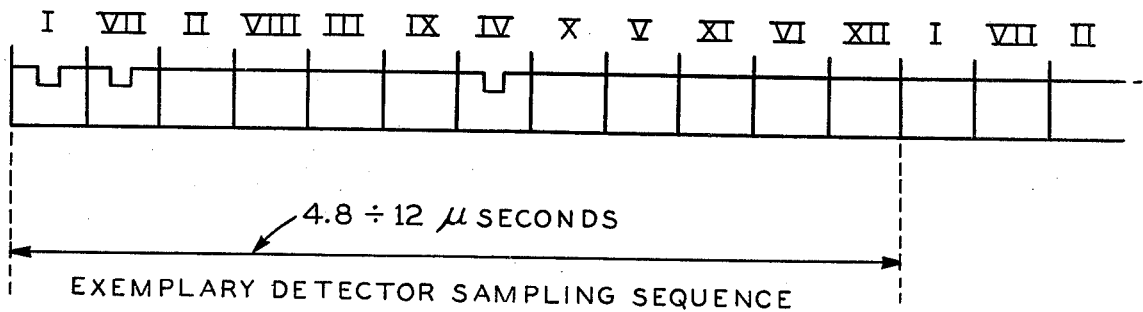
Figure 11E:
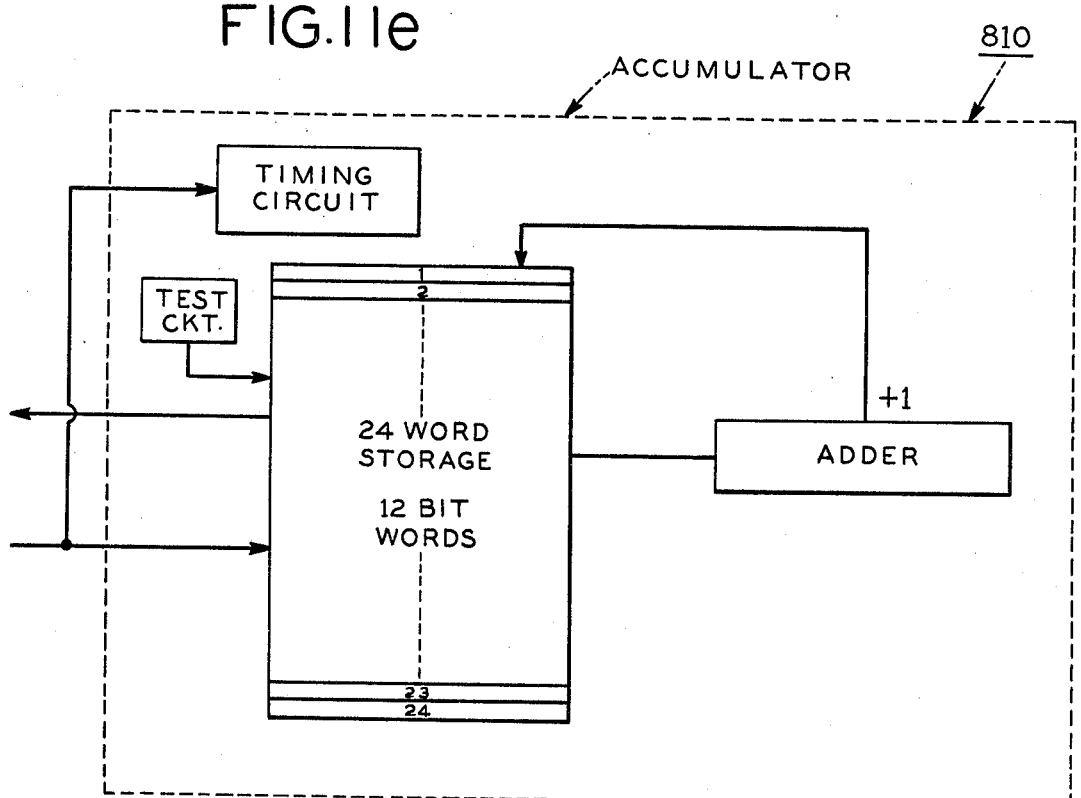
Figure 11F:
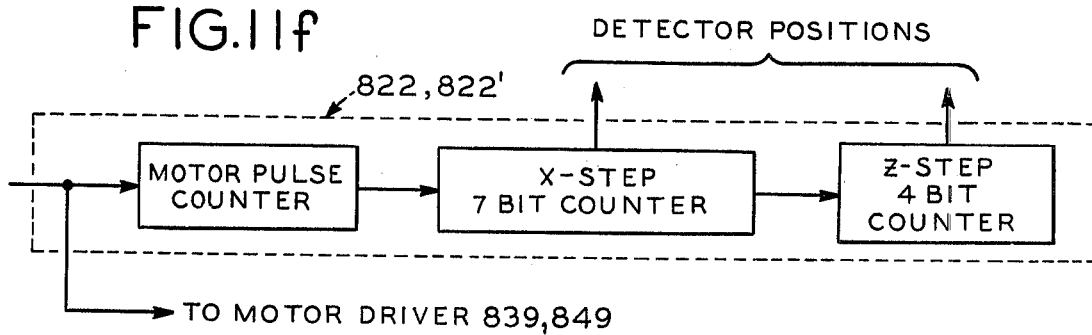

The general operation of the arrangement of FIG. 11 involves a computer 840 under program control which transmits memory address locations and commands, (address first followed by a command) through computer bus interface 843. The accumulator 810 and motor control 822 receive commands from the scanner data multiplexer 820 by way of UART 870 and transfer scintillation count data and other data, by way of UART 879 to the scanner data multiplexer 820 for appropriate addressing and transfer to computer 840, for example a Data General Exlipse S230 general purpose computer under program control. Timing diagrams for reference in connection with FIGS. 11 to (d) are shown in FIGS. 11(a), 11(b) and 11(c); the scanner data multiplexer 820 is shown schematically in FIG. 11(d). The computer processes the scintillation count data under program control as hereinabove described.

Scanner data multiplexer 820, under program control in computer 840, sends commands to data acquisition circuits for purposes of (1) controlling detector movement (2) controlling couch movement and (3) performing diagnostics. It receives from the data acquisition circuits (1) accumulated scintillation count data (2) system status information (3) diagnostic data. The scanner data multiplexer 820 calculates addresses for data to be deposited in computer memory in a method which optimally organizes the data in the high speed random access memroy for further processing by the computer.

The scanner data multiplexer 820 provides bi-directional communication between a general purpose stored program computer and (1) circuits in the scanner system which drive motors to control the location of detectors and the patient, (2) circuits in the system which accumulate scintillation counts from the detectors. The full duplex communication is implemented serially using a universal asynchronous receiver/transmitter interface (UART 870).

An exemplary communication format between the scanner data multiplexer 820 and the accumulator/motor driver circuits is shown below in Table A.

TABLE A

| Code | Command |
|------|---------|
| 0000 | System Reset |
| 0001 | Stop Scan/Slew Home |
| 0010 | Start Scan Line/Patient Data Mode |
| 0100 | Start Scan Line/Data Diagnostic Mode |
| 0101 | Start Scan Line/Address Diagnostic Mode |
| 0111 | Scanner Data Multiplexer Internal Test |
| 1000 | Calibrate Gain Adjust |
| 1001 | Couch Movement |

All of these commands are transmitted from the scanner data multiplexer 820 in eight bit bytes via the UART 870. The first five commands are transmitted in one byte with the format shown in FIG. 14(a).

The last three commands are two byte commands and are transmitted in the format shown in FIG. 14(b).

All commands transmitted from the scanner data multiplexer 820 have been sent to it by the host computer 840 and received on the computer bus 843 by the scanner data multiplexer 820 in the formats shown in FIG. 14(c).

Prior to transmitting a command, the scanner data multiplexer has received from the host computer 840 and has stored in its base address register 910 the starting address in computer memory for storing the status information and data which are received by the scanner data multiplexer 820 in response to the command.

Command and basic address information is recognized and accepted by the scanner data multiplexer 820 only when the device code decoder 821 decodes its predetermined device code as shown in bits 10-15 of FIG. 14(c).

If the command was a command to gather patient data or run diagnostics, the scanner data multiplexer, 820, upon receipt of the scanner data calculates an address for each transmission it receives. The format of the data receives by the scanner data multiplexer 820 is of the form shown in FIG. 14(d).

Status and error messages are loaded into the address in computer memory which is stored in the base address register 910 of the scanner data multiplexer 820.

Data associated with one of the detectors is loaded in to a $3072_{10}$ word buffer in the computer main memory.

All transfers from the scanner data multiplexer 820 into computer memory are via direct memory access. At the conclusion of transferring data into computer memory, the scanner data multiplexer 820 issues an interrupt request to the host computer 840 to notify the computer that the data deposited in computer memory is available for further processing.

The detector related data coming into the scanner data multiplexer 820 is associated with two channels from each of twelve detectors. The sequence of data is such that the data for one resolution element from one channel of each of the twelve detectors is received by the scanner data multiplexer 820.

Detector data is received sequentially from opposing detector pairs so that the sequence of detector data coming into the scanner data multiplexer 820 is as follows:

| | |
|---|---|
| CH 1 | Detector I |
| CH 1 | Detector VII |
| CH 1 | Detector II |
| CH 1 | Detector VIII |
| CH 1 | Detector III |
| CH 1 | Detector IX |
| CH 1 | Detector IV |
| CH 1 | Detector X |
| CH 1 | Detector V |
| CH 1 | Detector XI |
| CH 1 | Detector VI |
| CH 1 | Detector XII |
| CH 2 | Detector I |
| CH 2 | Detector VII |
| CH 2 | Detector II |
| CH 2 | Detector VIII |
| CH 2 | Detector III |
| CH 2 | Detector IX |
| CH 2 | Detector IV |
| CH 2 | Detector X |
| CH 2 | Detector V |
| CH 2 | Detector XI |
| CH 2 | Detector VI |
| CH 2 | Detector XII |

The address calculation circuits in the scanner data multiplexer 820 calculate addresses so that the same resolution element from each detector has a displacement in the 128 word buffer, associated with that detector, which corresponds to its displacement in the physical scanning pattern regardless of detector number or radial scanning step.

To accomplish this, two aspects of the detector motion patterns must be taken into account in calculating the correct location in computer memory for storing a resolution element: opposing detectors scan in opposite directions so that while incrementing the address for one detector, the address for the opposing detector is decremented or vice versa; the motions of all detectors are reversed for each radial increment in gathering data so that after each radial step the incrementing/decrementing patterns are reversed. During all of these operations, an appropriate offset must be included in the address calculation to provide for offsetting the data for each buffer by 128 locations in computer memory.

With reference to FIG. 11, the detectors I to XII are schematically shown in a line, with the direction of tangential travel for each detector indicated by the arrows above the detectors. The number "1" adjacent to the arrows indicates the first resolution element for the respective detectors while the number "128" indicates the last or 128th resolution element, in the preferred embodiment described herein. In operation, the scintillation developed by crystals 32 is converted to "counts" in photomultipliers 36, with discrimination being provided in pulse height analyzers 33 and a digital signal is delivered to high speed digital switch 800 which samples both channels of all detectors I–XII during an interval of, for example about 4.8 μ sec., so that on the order of 20,000 samplings of the detectors I–XII occurs during a resolution element. Two independent channels are provided in the pulse height analyzers 33 to provide capability for situations where a patient has been administered two isotopes of different radioactivity energy levels. In such an instance, the data for both conditions can be separately and concurrently spatially and intensity oriented and displayed spatially.

The binary data obtained by sampling is passed to accumulator 810, containing for example, a RAM memory, which accumulates the data in a sequence of detectors I–XII and transfers the data in a sequence of opposing detectors. For example, the sequence of transferred accumulated data can be detector I, detector VII, II, VIII; III, IX; IV, X; V, XI, VI, XII. Upon completion of a resolution element of travel for each detector, i.e. 1/128 of the scan line, the contents of the accumulator 810 are transferred into the scanning data multiplexer 820 wherein the data is received serially in the sequence of opposing detectors as described above, and addressed to the memory 830 of the general purpose computer 840 at contiguous buffer memory locations, as hereinafter described, in an orientation such that the opposite and reciprocal motion of opposed detectors, is compensated.

At the end of a scan line, i.e., 128 resolution elements, the words in the buffer memory locations are transferred to a magnetic disk and the completion of all the scan lines, e.g. 12, the magnetic disk contains all the scan line data for one "slice" in a form which facilitates reconstruction and the display of a picture as hereinabove described. The universal asynchronous receiver/transmitter interface, UART 870, provides commands under computer program control for the execution of the operations indicated in which the advance to the next command is signalled when the previous command has been completed.

Figure 11D:
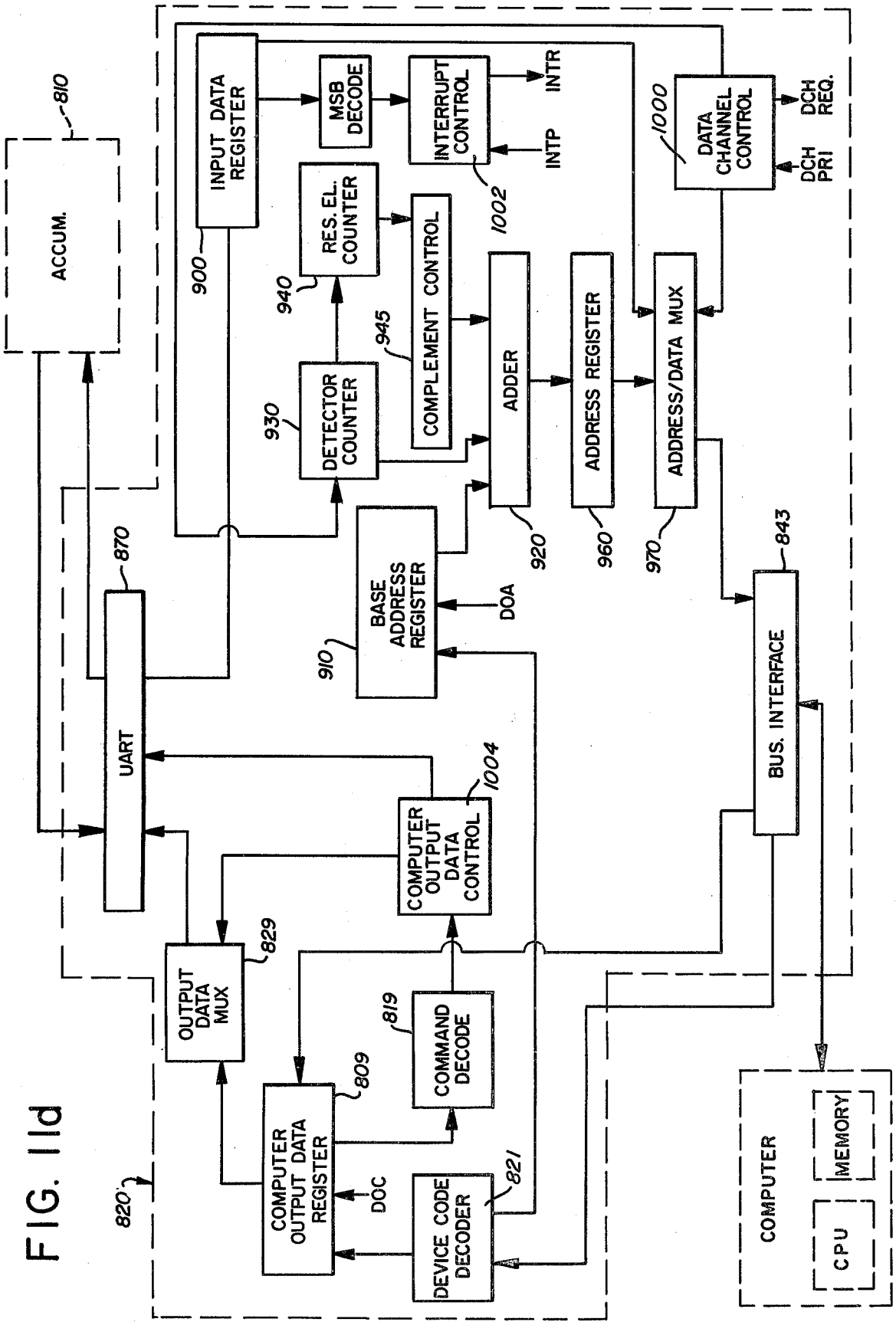
Figure 12:
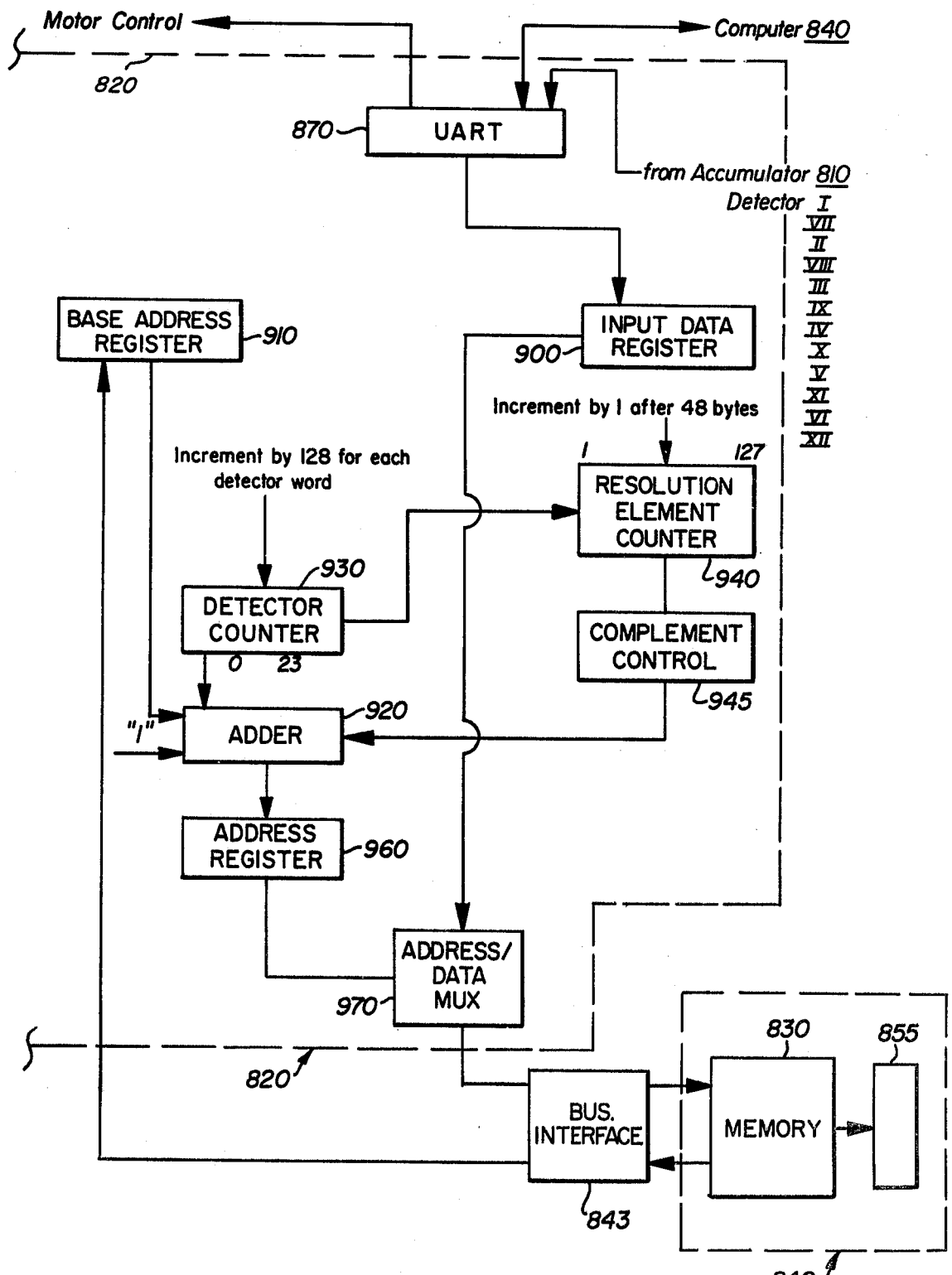

With reference to FIG. 12, which shows a relevant portion of the previously mentioned scanner data multiplexer 820 shown in FIG. 11(d), at the end of the first and every subsequent resolution element, the input data register 900 receives, from accumulator 810, shown schematically in a "burst" of 48 bytes from which it assembles 24 sixteen bit words—twelve words from each channel. The information in each of these words is for example, as shown in FIG. 14(d). This, for each resolution element, is in the sequence of opposed detectors, e.g., I, VI, II, VII, etc., with channel 1 data being followed by channel 2 data for a given detector. At the time that this burst of data is received by input data register 900, a base address, determined by the computer 840 under program control is in the base address register 910. This base address will be considered to be "4000" for purposes of convenience but can be any place in a high speed random access memory where a sufficient number of sequential memory address locations are available, e.g. 3072 (128 resolution elements × 12 scan lines × 2 channels) in the specific embodiments described herein.

Considering the first resolution element 1, all detectors I–XII are at the start of a scan line; adder 920 is at a level representing a 1 count whenever data is not being loaded into the memory address contained in the base address register. Detector counter 930 is at 0 for the first detector I in the sequence I, VI, II, VII, etc. and resolution element counter 940 is at 0 for the first resolution element. Thus, for this condition, the one count in the adder 920, which represents the relative address in this case, is added to the base address 4000 in adder 920 to establish an absolute address of "4001" in the absolute address register 960. This address followed by the scintillation count data for detector I in input register 900, a sixteen bit word, is transferred via a conventional address/data multiplexer 970 to memory 830 of computer 840. This transfer is via the computer's direct memory access channel for the presently described embodiments. With reference to FIG. 13, memory 830 comprises 24 storage buffers A, B,–M of 128 words each, for a total of 3072. For the first resolution element 1, the word representing the counts of the first detector in the sequence, detector I are stored in the first address location of buffer A shown at "4001".

Detector counter 930 is incremented by one, which provides an offset of 128, the total number of resolution elements, upon the entry of the data for detector I into memory, as previously described.

For detector VII, the second detector in the sequence I, VII, II, etc., detector counter 930 is at "1", being incremented upon the transfer of data from accumulator 810 and resolution counter 940 remains at "0"; for detector VII, (and every other subsequent detector in sequence, i.e. VIII, IX, X, XI and XII) the complement control 945 provides the complement of resolution counter 940 in adder 920. Thus, for detector VII, the complement 127 is added to 128 from the incremented detector counter 930, and 1 in the adder 920, to give 256 which is added to the base address to provide an address of 4256 in address register 960. This address followed by the count data in input register 900, a sixteen bit word, is transferred to memory 830 of computer 840. This as shown in FIG. 13 illustrates that the word representing the counts of the second detector in the sequence, detector VII, are stored in the last address location of buffer B shown at 4256. For the next, i.e. third detector in the sequence, detector II, detector counter 930 has been further incremented by one, to provide an offset by 128 to 256, which is added to the 1 in adder 920, to provide a relative address of 257, complement control 945 being inactive for detector II, as in the case of detector I. The address location for the word representing the "counts" of detector II for the first resolution element is 4257, the first address location in buffer C. For detector VIII, the next detector in the sequence, the detector counter 930 is further incremented one, to provide an offset by 128 to 384, which is added to the 1 in adder 920, and the complement 127, to provide a relative address of 512 for which the address location is 4512 the last address location in buffer D.

As can be seen, and with reference to FIG. 13, and Table B, the operation of scanner data multiplexer 820 provides for the loading of the adjacent buffers for opposing detectors from opposite directions. For example, the first word for detector I is loaded at the first address location in buffer A while the first word for the opposed detector VII is loaded in the last address in buffer B. The same opposite loading is seen for buffers C, D; E, F; G, H; J, K; L, M. At the end of the scan line, 128 resolution elements, all of the buffers A–M have been loaded in the manner described, as further shown in the exemplary Table B hereinbelow. Consequently, the contents of the memory 830 for a scan line can be transferred to a magnetic disk 855 in a sequence which constitutes a compensation for the opposite travel of the opposed detectors and subsequently processed by computer 840 as described hereinabove.

The above description was directed to the first of a plurality of scan lines, 12 in the embodiment being considered. For the second scan line, the detector travel is from resolution element 128 to 1 and for this scan line, the previously described interaction of adder 920, detector counter 930 and resolution element counter being incremented at the end of the scan line) except that complement control 945 provides a complement for the alternate detectors I, II, III, IV, V, VI instead of VII, VIII, IX, X, XI and XII.

That is to say, for the odd numbered scan lines, or odd numbered radial steps, first, third, etc., the complement control operation is the same; but the complement control is reversed for the even numbered scan lines.

pattern in all of the 3072 memory locations used for storing scintillation counts data. In checking out the memory loading process, the command seven is received on the computer bus 843 in the format of FIG. 14(c). Twelve bits follow, which can be any pattern, e.g. all "zeros", all "ones" or a "checker board" of "ones" and "zeros". A base address calculated by the computer 840, e.g. "4000" is established in base address register 910. The command is a 16 bit word, first the address, then the command which is received in output data register 809. The test pattern is the last twelve of the sixteen bits. The command is decoded at 819 and the 16 bit word in two 8 bit bytes is transferred by an output data multiplexer 829 to UART 870. For this command code, a test circuit turns the data around back into the UART 870 and then into portion of scanner data multiplexer shown in FIG. 12 and this data is manipulated in the manner previously described in connection with FIG. 12. This "checking" data, instead of having a detector identification, e.g. I, VII, II, VIII, etc., followed by scintillation data, is received as "code 7" followed by the test pattern generated by the computer 843. This data is addressed and stored in the buffers A–M of the computer memory in the same manner as described above in connection with FIG. 12 and all 3072 of the memory locations can accordingly be checked for the test pattern.

TABLE B

| CH 1 REL Address LOC | DET I I.D.SEQ CH 1 | DET II CH 1 | DET III CH 2 | DET V CH 2 | DET VI |
|---|---|---|---|---|---|
| ODD RADIAL "Z" STEPS | | | | | |
| 1 | 1 257 | 3 513 | 5 2561 | 21 2817 | 23 |
| 2 | 25 258 | 27 514 | 29 2562 | 45 2818 | 47 |
| 3 | 49 259 | 51 515 | 53 2563 | 69 2819 | 71 |
| 127 | — 3025 | — | — | — | — |
| — | — | — | — | — | — |
| — | — | — | — | — | — |
| 127 | 3025 383 | 3029 639 | 3029 2687 | 3045 2943 | 3047 |
| 128 | 3049 384 | 3051 640 | 3053 2688 | 3069 2944 | 3071 |
| 129 | 3050 385 | 3052 641 | 3054 2689 | 3070 2945 | 3072 |
| 130 | 3026 386 | 3028 642 | 3030 2690 | 3046 2946 | 3048 |
| — | — | — | — | — | — |
| — | — | — | — | — | — |
| 254 | 50 510 | 52 765 | 54 2814 | 70 3070 | 72 |
| 255 | 26 511 | 28 767 | 30 2815 | 46 3071 | 48 |
| 256 | 2 512 | 4 768 | 6 2816 | 22 3072 | 24 |
| CH 1 | DET VII CH 1 | DET VIII CH 1 | DET IX CH 2 | DET XI CH 2 | DET XII |
| EVEN RADIAL "Z" STEPS | | | | | |
| CH 1 REL Address LOC | DET I I.D. SEQ CH 1 | DET II CH 1 | DET III CH 2 | DET V CH 2 | DET VI |
| 1 | 3049 257 | 3051 513 | 3053 2561 | 3069 2817 | 3071 |
| 2 | 3025 258 | 3027 514 | 3029 2562 | 3045 2818 | 3047 |
| 3 | 3001 259 | 3003 515 | 3005 2563 | 3021 2819 | 3023 |
| — | — | — | — | — | — |
| — | — | — | — | — | — |
| 127 | 25 383 | 27 659 | 29 2687 | 45 2943 | 47 |
| 128 | 1 384 | 3 640 | 5 2688 | 21 2944 | 23 |
| 129 | 2 385 | 4 641 | 6 2689 | 22 2945 | 24 |
| 130 | 26 386 | 28 642 | 30 2690 | 46 2946 | 48 |
| — | — | — | — | — | — |
| — | — | — | — | — | — |
| 254 | 3002 510 | 3004 766 | 3006 2814 | 3022 3070 | 3024 |
| 255 | 3026 511 | 3028 767 | 3030 2815 | 3046 3071 | 3045 |
| 256 | 3050 512 | 3052 768 | 3054 2816 | 3070 3072 | 3072 |
| CH 1 | DET VII CH 1 | DET VIII CH 1 | DET IX CH 2 | DET XI CH 2 | DET XII |

In addition to the foregoing calculation of absolute addresses for the scintillation count data, the scanner data multiplexer 820 has the capability to provide for checking out the memory loading process, accumulations process and motor drive operation.

In the case of checking out the memory loading process, the scanner data multiplexer 820, shown in FIG. 11(d) checks the ability to deposit a particular variable For checking the accumulation process, the scanner data multiplexer 820 checks the ability of accumulator 810 to transfer data in the desired sequence of opposed detectors I-VII, II-VIII, etc. In this instance the command "four" is received on the computer bus 843 in the format of FIG. 14(a), and is received in output data register 809. A base address, e.g. "4000" is established in base address register 910; calculated by the computer 840. The command is decoded at 819 and one 8 bit byte, (base address, code four) is transferred by an output data multiplexer 829 to UART 870 which transmits the command four to accumulator 810 which, when it receives a command four, causes a timing circuit to trigger a test circuit which feeds the accumulator 810. The accumulator 810 generates either a $2525_8$ pattern for one PHA channel and a $5252_8$ pattern for the other PHA channel or vice versa, as determined by the timing circuit. The accumulator 810, in the present instance, accumulates data by adding "one" whenever the input thereto is true. The accumulated data is then transmitted via UART 870 to the scanner data multiplexer arrangement of FIG. 12 as in the case of actual operation as described previously in connection with FIG. 12; the first four bits of each word will be a detector identification "I", etc., in the sequence of opposing detectors, followed by 1536 words of 2-5-2-5 and 1536 words of 5-2-5-2. These data words are addressed and transferred to the buffers A-M and A'-M' shown in FIG. 13 and buffers A-M receive 1536 words of 2-5-2-5 and A'-M' receive 1536 words of 5-2-5-2 (or vice versa) as a check of the accumulation.

For checking the motor counters 822 and 822', the scanner data multiplexer 820 checks the ability of the X-drive counter 822 to count to 128 (from 0 to 127 and the ability of the Z-drive counter 822' to count to 12 (0-11) and provide counts in the 3072 contiguous buffer locations previously noted. In this instance, command "5" is received on the computer bus 843 in the format of FIG. 14(a) and is received in output register 809. A base address, e.g. "4000" is established in base address register 910; the command is decoded at 819 and one 8 bit byte is transferred by an output data multiplexer 829 to UART 870 which transmits the command "5" to counters 822 and 822'' which step from 0 to 127 and 0-11 respectively. For command "5" this data, the state of these counters, is transferred to the output register of accumulator 810, where scintillation data would ordinarily go. The counter data is then transmitted via UART 870 to the scanner data multiplexer arrangement of FIG. 12 as in the case of actual operation as described previously in connection with FIG. 12; the first four bits of each word will be a detector identification "I", etc., in the sequence of opposing detectors, followed by 1536 words and another 1536 words, reflecting the state of counters 822, 822', for a total of 3072. These data words are addressed and transferred to the buffers A-M and A'-M' of FIG. 13 as a check of the counters 822, 822'.

In the general purpose computer hereinbefore mentioned with reference to FIG. 11, the Data Channel Control 1000, Interrupt Control 1002, Computer Data Output Control 1004 are conventional arrangements for arbitrating priority and providing interruptions.

FIG. 8 shows a display obtained through the practice of the above-described preferred embodiment of the present invention. The display shows "slices" 3-6, 2-5 minute per slice with the radionuclide being 99 m$_{TC}$.

Particular advantages of the imaging device of the present invention are the ability, due to the ultrahigh sensitivity provided, to permit early diagnosis of pathological changes and images can be obtained which show accurately the location and shape of abnormalities. Also, images can be conveniently retrieved and a plurality of transaxial slices can be readily obtained with each taking from 2-5 minutes. Further, high target to background images can be readily obtained with excellent functional detail due to the use of highly focused collimators in the manner of the present invention; in addition dual pharmaceutical studies can be readily performed simultaneously.

The mechanical implementation is such that the entire system can be accomodated in a 16'×16' room. Importantly, the scanning pattern with the use of highly focused collimators, enables the use of collimators of quite short focal length, i.e. the focal length need be only about $\frac{1}{2}$ the diameter of the total scan field. Moreover, the continuous and essentially constant close adjacency of the highly focused collimators throughout the scanning operation enables optimum collection of patient emitted radiation e.g. not more than about 15% of the scan field is outside the included angles of the collimator's array; this space being permitted in order to provide for adequate lead shielding of the scintillation crystals.

While the foregoing description has been particularly directed to the spatial location and intensity of emitted radiation from fixed locations in a patients head, the present invention, can, be used, with routine modifications, as will be recognized by those skilled in the art, for other body organs.

What is claimed is:

1. A scanning apparatus for an array of highly focused collimators comprising a base plate having (i) a plurality of first tangent drive slots arranged symmetrically about and equidistant from an axis normal to said base plate with each slot being tangent to a common circle centered on said axis (ii) a first prime mover drive slot parallel to one of said tangent drive slots and spaced further from said axis than said parallel tangent slot; a rotatable disk member rotatably engaged to said base plate on one side thereof being rotatable about said normal axis, said disk member having (i) a plurality of equally angularly spaced radially extending translation slots each of which overlaps one of said tangent drive slots (ii) a driver member affixed to said disk having a radially extending slot outward from and in alignment with one of said translation slots and overlapping said first prime mover drive slot; a plurality of equally angularly spaced radially aligned guide means mounted on said base plate on the side opposite from said disk, each of said guide means being arranged opposite and extending in a direction normal to one of said tangent drive slots, with alternate guide means being located radially inward from said tangent drive slots and the remaining guide means being located radially outward from said tangent drive slots; a plurality of track members respectively arranged transverse to and slidably mounted on said guide means; a plurality of carriages respectively mounted on said track means, the carriages mounted on radially inward guide means having outwardly extending slotted members parallel to said guide means and arranged overlapping a respective tangent drive slot and the carriages mounted on radially outward guide means having inwardly extending slotted members parallel to said guide means and arranged overlapping a respective tangent drive slot; a drive block slidably mounted in each tangent drive slot and engaging an overlapping slotted member of a carriage on one end and an overlapping translation slot of the disk member on the other end, a prime mover drive block slidably mounted in the first prime mover drive slot engaged to the radially extending overlapping slot of said driver member; first driving means engaged to said first prime mover drive block to cause said prime mover drive block to travel a predetermined distance in said first prime mover drive slot and rotate said disk member and impart a predetermined tangential travel motor to said carriages; a plurality of engaged adjacently oppositely rotating bevel gears arranged radially inward from said tangential drive slots and said track members, each of said bevel gears being respectively engaged to a radially adjacent track member by a threaded coupling for imparting alternate inward and outward radial motion to said track members; second driving means engaged to a threaded coupling of only one said threaded coupling; and a plurality of inwardly focused collimators respectively mounted on said carriages to provide a circular array of closely adjacent collimators when said track means are at a predetermined common distance from said tangent drive slots and said carriages are centered with respect to their respective predetermined tangential travel.

* * * * *